United States Patent [19]

Burjes et al.

[11] Patent Number: 4,755,311

[45] Date of Patent: Jul. 5, 1988

[54] PHOSPHORUS-, SULFUR- AND BORON-CONTAINING COMPOSITIONS, AND LUBRICANT AND FUNCTIONAL FLUID COMPOSITIONS CONTAINING SAME

[75] Inventors: Louis Burjes, Wickliffe; Stephen A. DiBiase, Euclid, both of Ohio

[73] Assignee: The Lubrizol Corporation, Wickliffe, Ohio

[21] Appl. No.: 896,539

[22] Filed: Aug. 14, 1986

[51] Int. Cl.$^4$ ............... C10M 137/10; C10M 139/00
[52] U.S. Cl. .................. 252/49.9; 252/46.7; 252/49.3; 252/49.6; 252/78.5; 252/32.7 E; 252/34; 558/72
[58] Field of Search ............... 252/49.6, 78.5, 46.7, 252/49.9; 558/72

[56] References Cited

U.S. PATENT DOCUMENTS

| | | | |
|---|---|---|---|
| 2,063,629 | 12/1936 | Salzberg et al. | 260/99.20 |
| 2,146,584 | 2/1939 | Lipkin | 87/9 |
| 2,197,835 | 4/1940 | Reiff | 87/9 |
| 2,224,695 | 12/1940 | Prutton | 148/6.5 |
| 2,364,284 | 12/1944 | Freuler | 252/39 |
| 2,413,852 | 1/1947 | Turner | 252/49.9 |
| 2,447,288 | 8/1948 | Smith et al. | 260/461 |
| 2,597,534 | 5/1952 | Schrader | 260/461 |
| 2,605,226 | 7/1952 | Vaughn | 252/49.9 |
| 2,616,905 | 11/1952 | Asseff et al. | 260/399 |
| 2,647,140 | 7/1953 | Jonas | 260/461 |
| 2,795,549 | 6/1957 | Abbott et al. | 252/49.7 |
| 2,824,115 | 2/1958 | Beacham et al. | 260/429.5 |
| 2,919,979 | 1/1960 | Martin et al. | 44/63 |
| 2,995,596 | 8/1961 | Debo | 260/461 |
| 3,033,789 | 5/1962 | Asseff | 252/49.9 |
| 3,087,936 | 4/1963 | LeSuer | 260/326.3 |
| 3,115,398 | 12/1963 | Thayer | 44/66 |
| 3,119,853 | 1/1964 | Reetz et al. | 558/72 |
| 3,150,094 | 9/1964 | DeYoung et al. | 558/72 |
| 3,172,892 | 3/1965 | LeSuer et al. | 260/326.5 |
| 3,198,817 | 8/1965 | Langer | 260/429.1 |
| 3,219,666 | 11/1965 | Norman et al. | 260/268 |
| 3,265,618 | 8/1966 | Henderson et al. | 252/32.5 |
| 3,272,746 | 9/1966 | LeSuer et al. | 252/17.5 |
| 3,284,409 | 11/1966 | Dorer | 252/49.9 |
| 3,294,874 | 12/1966 | Schrader | 260/948 |
| 3,318,811 | 5/1967 | Conradi et al. | 252/49.9 |
| 3,347,790 | 10/1967 | Meinhardt | 252/32.5 |
| 3,350,316 | 10/1967 | Berger et al. | 558/72 |
| 3,355,270 | 11/1967 | Amick et al. | 44/68 |
| 3,357,920 | 12/1967 | Nacson | 252/49.9 |
| 3,484,375 | 12/1969 | Hu | 252/49.9 |
| 3,489,682 | 1/1970 | LeSuer | 252/32.7 |
| 3,493,508 | 2/1970 | Andress, Jr. | 252/42.7 |
| 3,510,426 | 5/1970 | Papay | 252/46.6 |
| 3,513,093 | 5/1970 | LeSuer | 252/32.5 |
| 3,632,637 | 1/1972 | Martell | 260/519 |
| 3,654,155 | 4/1972 | Braid | 558/72 |
| 3,909,429 | 9/1975 | McClaflin | 252/46.7 |
| 3,984,448 | 10/1976 | Lippsmeier | 260/429 R |
| 4,028,390 | 6/1977 | Rubino et al. | 260/429.3 |
| 4,077,941 | 3/1978 | Stephen et al. | 260/45.75 N |
| 4,089,793 | 5/1978 | Meinhardt | 252/32.7 E |
| 4,093,614 | 6/1978 | Chibnik et al. | 260/299 |
| 4,118,328 | 10/1978 | Hooten | 252/32.5 |
| 4,207,195 | 6/1980 | Horodysky | 252/46.6 |
| 4,338,205 | 7/1982 | Wisotsky | 252/32.5 |
| 4,431,552 | 2/1984 | Saletine | 252/32.7 |
| 4,529,528 | 7/1985 | Horodysky | 252/49.6 |
| 4,536,306 | 8/1985 | Horodysky et al. | 558/72 |
| 4,555,497 | 11/1985 | Coleman, III et al. | 502/115 |

OTHER PUBLICATIONS

Reetz, "Trialkyl Phosphite Borines. A New Type of Phosphorus-boron Cpd", 10-60, pp. 5039-5042, Jour. Am. Chem. Soc. vol. 82.

Primary Examiner—William R. Dixon, Jr.
Assistant Examiner—Ellen McAvoy
Attorney, Agent, or Firm—James L. Cordek; Denis A. Polyn; Joseph P. Fischer

[57] ABSTRACT

This invention is directed to borated amine salts of dihydrocarbyl monothiophosphoric acids, and to lubricating and functional fluid compositions containing said borated amine salts. The lubricating and functional fluid compositions have improved extreme pressure properties and high temperature stability.

The borated amine salts of the invention may be characterized by the formula

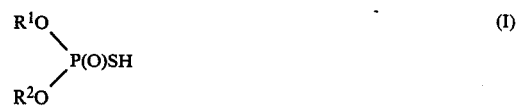

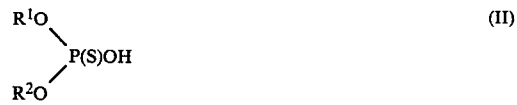

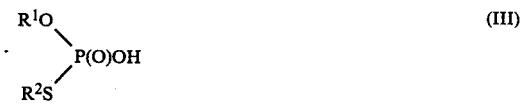

or mixtures thereof wherein $R^1$ and $R^2$ are each independently hydrocarbyl groups containing from 1 to about 30 carbon atoms. In one preferred embodiment, the amine salts are derived from hydroxyhydrocarbyl amines.

The lubricating and functional fluid compositions may contain, in addition to the borated amine salts, at least one nitrogen-containing composition prepared by the reaction of a hydrocarbon-substituted succinic acid-producing compound with at least about one-half equivalent, per equivalent of acid-producing compound, of an amine containing at least one hydrogen attached to a nitrogen atom. The lubricating compositions of the present invention are particularly useful as lubricating oils, functional fluids and greases.

56 Claims, No Drawings

PHOSPHORUS-, SULFUR- AND BORON-CONTAINING COMPOSITIONS, AND LUBRICANT AND FUNCTIONAL FLUID COMPOSITIONS CONTAINING SAME

TECHNICAL FIELD OF THE INVENTION

This invention relates to borated amine salts of monothiophosphoric acids, and to lubricating oils and functional fluid compositions containing these salts which have improved high temperature stability and which are useful for lubricating moving metal surfaces which are in contact with each other. The functional fluids may be hydrocarbon-based or aqueous-based. More particularly, the invention relates to borated amine salts and lubricating compositions containing said salts which may be lubricating oils useful in automotive transmissions and axles.

BACKGROUND OF THE INVENTION

The problems associated with the lubrication of gears such as utilized in automotive transmission and axles are well known to those skilled in the art. In the lubrication of automatic transmissions, proper fluid viscosity at both low and high temperatures is essential to successful operation. Good low temperature fluidity eases cold weather starting and insures that the hydraulic control system will properly "shift gears". High viscosity at elevated temperatures insures pumpability and the satisfactory operation of converters, valves, clutches, gears and bearings. These conflicting fluidity requirements require a product that exhibits the following characteristics:
(a) high temperature viscosity retention,
(b) low temperature fluidity,
(c) shear stability, and
(d) high temperature stability.

In order to prepare lubricants having these characteristics, it has become common practice to add a variety of chemicals to the lubricating oil. For example, in order to meet the viscosity requirements, compositions have been added to the oils which are characterized by relatively small change in their viscosity with changing temperature. In general, lubricants containing such compositions have the desirable properties of functioning immediately, even though cold, upon being put into service, and to continue to function satisfactorily as they become heated during operation. Commonly used gear oil viscosity improvers include polymethacrylates and polyolefins.

In addition to viscosity improvers, lubricating compositions useful as gear lubricants generally will contain pour point depressants, extreme pressure agents, oxidation inhibitors, corrosion inhibitors, foam inhibitors, and friction modifiers.

Lubricating compositions have been suggested containing various nitrogen-containing and phosphorus-containing compositions to impart desirable properties to lubricating compositions. for example, U.S. Pat. No. 3,513,093 describes lubricant compositions containing substituted polyamines which comprise the reaction product of an alkylene amine with a substantially hydrocarbon-substituted succinic acid and at least about 0.001 mole of a phosphorus acid-producing compound selected from the group consisting of phosphoric acids, phosphorous acids, phosphonyl acids, phosphinyl acids, and the esters, the halides and the anhydrides thereof. The phosphorus acids may contain one or more sulfur atoms attached to the phosphorus atom. The substituted polyamines are useful as anti-wear agents, anti-rust agents, detergents, etc. U.S. Pat. No. 4,338,205 describes a lubricating oil with improved diesel dispersancy. The lubricating oils contain an acid-treated, oil-soluble alkenyl succinimide or a borated alkenyl succinimide which has been treated at an elevated temperature with an oil-soluble strong acid such as an alkyl sulfonic acid, or a phosphoric acid. The oil-soluble organic acids are generally classified as those acids containing a hydrogen-phosphorus moiety which has a pK of −10 to about +5.0.

The preparation of salts, both metal salts and ammonium salts of dialkylmonothiophosphoric acids has been described in the art. For example, U.S. Pat. No. 2,647,140 describes a process for preparing dialkylthiophosphates by reacting a dialkylphosphite with sulfur and ammonia or an organic amine. The product is an ammonium salt of a dialkylthiophosphate.

The preparation of O-alkyl-O-cycloalkyl-S-alkyl thiophosphoric acid esters is described in U.S. Pat. No. 3,294,874. The process involves initially forming ammonium salts of O,O-dialkylthiophosphoric acids, and it is suggested that the product characterized by the following formulae which are in equilibrium

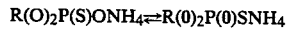

$$R(O)_2P(S)ONH_4 \rightleftharpoons R(O)_2P(O)SNH_4$$

the ammonium salts then are alkylated to form the desired S-alkylthiophosphoric acid esters.

The use of amine and metal salts of dialkylmonothiophosphoric acids in lubricating compositions also is described in the art such as in the following U.S. Pat. Nos.: 2,063,629; 2,224,695; 2,447,288; 2,616,905; 3,984,448; 4,431,552. Some of the above patents differ in the description of the alkyl groups and/or the nature of the metal or amine. For example, in U.S. Pat. No. 3,984,448, the alkyl groups contain from 1 to 6 carbon atoms, and in U.S. Pat. No. 2,447,288, the alkyl groups contain at least 5 carbon atoms. In U.S. Pat. No. 2,447,288, the amine used to form the amine salt is an aliphatic primary amine containing at least 8 carbon atoms, and in U.S. Pat. No. 2,063,629, the amine may be ammonia or a primary, secondary or tertiary amine.

Another publication which discusses the preparation of salts of dialkylthiophosphoric acids is Pesin, V. G. and Khaletskii, A. M., *Zhurnal Obshchei Khimii*, 31, No. 8, pp. 2508–2515, August, 1961. It is therein suggested that the salts of dialkylthiophosphoric acids are useful in the synthesis of insecticides, fungicides, bactericides, medicinal products, etc.

More recently, new demands are being placed on lubricants to be used in gear applications. Increases in commercial vehicle power and loading require the lubricant to be available to withstand severe thermal stressing while protecting the equipment being lubricated. Thus, the high temperature stability (e.g., above about 160° C.) of lubricants designed for gear applications is a significant consideration.

SUMMARY OF THE INVENTION

This invention is directed to borated amine salts of dihydrocarbyl monothiophosphoric acids, and to lubricating and functional fluid compositions containing said borated amine salts. The lubricating and functional fluid compositions have improved extreme pressure properties and high temperature stability.

The borated amine salts of the invention may be characterized by the formula

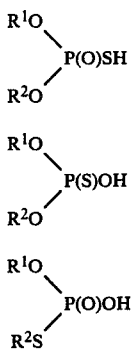

or mixtures thereof wherein $R^1$ and $R^2$ are each independently hydrocarbyl groups containing from 1 to about 30 carbon atoms. In one preferred embodiment, the amine salts are derived from hydroxyhydrocarbyl amines.

The lubricating and functional fluid compositions may contain, in addition to the borated amine salt, at least one nitrogen-containing composition prepared by the reaction of a hydrocarbon-substituted succinic acid-producing compound with at least about one-half equivalent, per equivalent of acid-producing compound, of an amine containing at least one hydrogen attached to a nitrogen atom. The lubricating compositions of the present invention are particularly useful as lubricating oils, functional fluids and greases.

The invention also relates to aqueous systems containing the borated amine salts compositions of the invention.

DESCRIPTION OF THE PREFERRED EMBODIMENTS (A) Borated Amine Salts of Monothiophosphoric Acid Compositions The borated amine salts of the present invention are borated amine salts of at least one dihydrocarbyl monothiophosphoric acid. The monothiophosphoric acids may be characterized by one or more of the following formulae

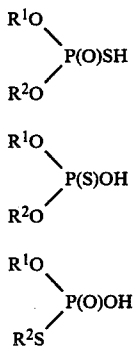

wherein $R^1$ and $R^2$ are each independently hydrocarbyl groups containing from 1 to about 30 carbon atoms.

As used in the specification and appended claims, the terms "hydrocarbyl" or "hydrocarbon-based" denote a group having a carbon atom directly attached to the remainder of the molecule and having predominantly hydrocarbon character within the context of this invention. Such groups include the following:

(1) Hydrocarbon groups; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule (that is, any two indicated substituents may together form an alicyclic group). Such groups are known to those skilled in the art. Examples include methyl, ethyl, octyl, decyl, octadecyl, cyclohexyl, phenyl, etc.

(2) Substituted hydrocarbon groups; that is, groups containing non-hydrocarbon substituents which, in the context of this invention, do not alter the predominantly hydrocarbon character of the group. Those skilled in the art will be aware of suitable substituents. Examples include halo, hydroxy, nitro, cyano, alkoxy, acyl, etc.

(3) Hetero groups; that is, groups which, while predominantly hydrocarbon in character within the context of this invention, contain atoms other than carbon in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbyl group.

Terms such as "alkyl-based group", "aryl-based group" and the like have meaning analogous to the above with respect to alkyl and aryl groups and the like.

The hydrocarbyl groups $R^1$ and $R^2$ may be the same or different hydrocarbyl groups, and generally, the total number of carbon atoms in $R^1$ and $R^2$ will be at least about 4. In a preferred embodiment the hydrocarbyl groups will contain from 4 to about 30 carbon atoms each, and preferably from about 8 to about 20 carbon atoms each. The hydrocarbyl groups $R^1$ and $R^2$ may be aliphatic or aromatic such as alkyl, aryl, alkaryl, aralkyl and alicyclic hydrocarbon groups. Examples of $R^1$ and $R^2$ groups include ethyl, n-butyl, n-hexyl, 2-ethylhexyl, 1-nonyl, 1-decyl, 1-dodecyl, 1-tetradecyl, stearyl, 1-hexadecyl, 1-octadecyl, oleyl, linoleyl, linolenyl, phytyl, myricyl, lauryl, cetyl, behenyl, etc. Examples of aromatic hydrocarbyl groups include phenyl, octylphenyl, nonylphenyl, and groups derived from similarly alkylated naphthols. Examples of alicyclic hydrocarbons include cyclohexyl, methylcyclohexyl, etc.

The $R^1$ and $R^2$ groups may each comprise a mixture of hydrocarbyl groups derived from commercial alcohols. Higher synthetic monohydric alcohols of the type formed by Oxo process (e.g., 2-ethylhexyl), the Aldol condensation, or by organo aluminum-catalyzed oligomerization of alpha-olefins (especially ethylene), followed by oxidation and hydrolysis, also are useful. Examples of some preferred monohydric alcohols and alcohol mixtures include the commercially available "Alfol" alcohols marketed by Continental Oil Corporation. Alfol 810 is a mixture containing alcohols consisting essentially of straight chain, primary alcohols having from 8 to 10 carbon atoms. Alfol 12 is a mixture comprising mostly $C_{12}$ fatty alcohols. Alfol 1218 is a mixture of synthetic, primary, straight-chain alcohols having 12 to 18 carbon atoms. The Alfol 20+ alcohols are mixtures of $C_{18}$-$C_{28}$ primary alcohols having mostly, on an alcohol basis, $C_{20}$ alcohols as determined by GLC (gas-liquid-chromatography). The Alfol 22+ alcohols are $C_{18}-C_{28}$ primary alcohols having mostly, on an alcohol basis, $C_{22}$ alcohols. These Alfol alcohols can contain a fairly large percentage (up to 40% by weight) of paraffinic compounds which can be removed before the reaction if desired.

Another example of a commercially available alcohol mixture is Adol 60 which comprises about 75% by weight of a straight chain $C_{22}$ primary alcohol, about 15% of a $C_{20}$ primary alcohol and about 8% of $C_{18}$ and $C_{24}$ alcohols. Adol 320 comprises predominantly oleyl alcohol. The Adol alcohols are marketed by Ashland Chemical.

A variety of mixtures of monohydric fatty alcohols derived from naturally occurring triglycerides and ranging in chain length of from $C_8$ to $C_{18}$ are available from Procter & Gamble Company. These mixtures contain various amounts of fatty alcohols containing mainly 12, 14, 16, or 18 carbon atoms. For example, CO-1214 is a fatty alcohol mixture containing 0.5% of $C_{10}$ alcohol, 66.0% of $C_{12}$ alcohol, 26.0% of $C_{14}$ alcohol and 6.5% of $C_{16}$ alcohol.

Another group of commercially available mixtures include the "Neodol" products available from Shell Chemical Co. For example, Neodol 23 is a mixture of $C_{12}$ and $C_{13}$ alcohols; Neodol 25 is a mixture of $C_{12}$ and $C_{15}$ alcohols; and Neodol 45 is a mixture of $C_{14}$ and $C_{15}$ linear alcohols. Neodol 91 is a mixture of $C_9$, $C_{10}$ and $C_{11}$ alcohols.

Fatty vicinal diols also are useful and these include those available from Ashland Oil under the general trade designation Adol 114 and Adol 158. The former is derived from a straight chain alpha olefin fraction of $C_{11}-C_{14}$, and the latter is derived from a $C_{15}-C_{18}$ fraction.

The borated amine salts may be derived from amines characterized by the formula $$R^3R^4R^5N$$

wherein each of $R^3$, $R^4$ and $R^5$ are independently hydrogen, hydrocarbyl, aminohydrocarbyl, hydroxyhydrocarbyl, or hydroxyhydrocarbyloxyhydrocarbyl groups or $R^3$ and $R^4$ may be hydrocarbyl groups joined together to form a ring including the nitrogen atom, and optionally, oxygen, sulfur, phosphorus or other nitrogen atoms. Thus, the amine salt may be derived from ammonia or a primary, secondary or tertiary amine. In one preferred embodiment, the salt is derived from a primary amine, and in another preferred embodiment, the salt is derived from a hydroxyhydrocarbyl amine. When the groups $R^3$, $R^4$ and/or $R^5$ are hydrocarbyl groups, they are generally hydrocarbyl groups containing up to about 150 carbon atoms and will more often be aliphatic hydocarbyl groups containing from about 4 to about 30 carbon atoms.

Alternatively, the borated amine salts may be derived from an acylated nitrogen compound prepared by reacting a carboxylic acid-producing compound with at least about one-half equivalent, per equivalent of the acid-producing compound, of an amine containing at least one hydrogen attached to the nitrogen atom. In one preferred embodiment, the acylated nitrogen compound may be any of the acylated nitrogen compounds or borated acylated nitrogen compounds described below as component (B). In such instances, the compositions of the present invention will comprise a mixture of (A) at least one amine salt of at least one monothiophosphoric acid wherein the salt is derived from an acylated amine (or borated acylated amine), and as a separate component, (B) at least one nitrogen-containing compound as described more fully below.

The borated amine salts of the monothiophosphoric acids of the present invention may be prepared by any one of the several techniques known in the art. For example, the amine salts may be prepared from the reaction of monothiophosphoric acid with amines followed by reaction with a boron compound, or the monothiophosphoric acid can be reacted with a borated amine. This procedure for preparing amine salts is described in, for example, U.S. Pat. No. 2,447,288.

In a preferred embodiment, the borated amine salts of monothiophosphoric acids are prepared from a dihydrocarbylphosphite a sulfur source, an amine and a boron compound. The dihydrocarbylphosphite may be characterized by the formula

         (IV)

wherein $R^1$ and $R^2$ are as described with respect to Formulae I–III. The monothiophosphoric acid of the amine salts obtained from the reaction of the phosphite (IV) with a sulfur source in the presence of an amine may be characterized by either Formula I, Formula II or Formula III, or mixtures thereof. It has been discovered that by control of the temperature of the reaction, product mixtures comprising either salts predominantly derived from Formulae I or II, or predominantly derived from Formula III can be obtained. At lower temperatures, salts of Formulae I and II will predominate and at higher temperatures, generally above 80° C., salts of Formula III begin to predominate due to a rearrangement from a P=S or P—S—H group to an R—S—P group. Generally, the temperature at which the rearrangement occurs will be dependent upon a number of factors such as the size and nature of the $R^1$ and $R^2$ groups, and on the nature and size of the amino compound or the metal compound used in the reaction. It has been observed, for example, that as the molecular weight of the hydrocarbyl groups $R^1$ and/or $R^2$ increases, the temperature required to effect the rearrangement also increases. Generally, rearrangement occurs at temperatures above 80° or 90° C. and most often above 110° C. The extent of rearrangement, and therefore the concentration of the R—S—P compound (III) present in the product mixture can be increased by conducting the reaction at higher temperatures and/or for longer periods of time. The amounts of the products identified by Formulae I and III present in the product of the reaction at any time during the reaction or at the end of the reaction can be determined readily by the use of $^{31}$phosphorus NMR.

The dihydrocarbylphosphites (IV) which are useful in the preparation of the amine and metal salts utilized in the present invention may be prepared by techniques well known in the art, and many dihydrocarbylphosphites are available commercially. In one method of preparation, a lower molecular weight dialkyl phosphite (e.g., dimethyl) is reacted with a higher molecular weight alcohol (e.g., decyl alcohol), and the decyl groups replace the methyl groups (analogous to classic transesterification) with the formation of methanol which is stripped from the reaction mixture.

The following is a specific example of the preparation of a dihydrocarbylphosphite wherein the hydrocarbyl groups contain an average of from about 8 to about 10 carbon atoms.

EXAMPLE P-1

A mixture of 1752 parts (12 moles) of Alfol 8-10 and 660 parts (6 moles) of dimethylphosphite is heated to about 120°–130° C. while sparging with nitrogen. The mixture is held at this temperature for about 8 hours while removing methanol as it is formed. The reaction mixture is vacuum stripped to 140° C. at 30 mm. Hg. The residue is filtered at about room temperature, and the filtrate is the desired product containing 10.3% phosphorus (theory, 9.2).

The sulfur source which is utilized in the preparation of the monothiophosphoric acid salts can be any of a variety of materials which are capable of supplying sulfur to the reaction. Examples of useful sulfur sources include elemental sulfur, sulfur halides, combinations of sulfur or sulfur oxides with hydrogen sulfide, and various sulfurized organic compounds as described below. Elemental sulfur is a readily available, useful and reactive sulfur source. The sulfur halides which are useful include sulfur monochloride, sulfur dichloride, etc. Combinations of sulfur and sulfur oxides (such as sulfur dioxide), with hydrogen sulfide also are useful sulfur sources.

The sulfurized organic compounds utilized as the sulfur source in preparing the monothiophosphoric acid salts of the present invention may be aromatic and alkyl sulfides such as dibenzyl sulfide, dixylyl sulfide, dicetyl sulfide, diparaffin wax sulfide and polysulfide, cracked wax oleum sulfides, etc. One method of preparing the aromatic and alkyl sulfides includes the condensation of a chlorinated hydrocarbon with an inorganic sulfide whereby the chlorine atom from each of two molecules is displaced, and the free valence from each molecule is joined to a divalent sulfur atom. Generally, the reaction is conducted in the presence of elemental sulfur.

Examples of dialkenyl sulfides which are useful in the compositions of the present invention are described in U.S. Pat. No. 2,446,072. These sulfides can be prepared by interacting an olefinic hydrocarbon containing from 3 to 12 carbon atoms with elemental sulfur in the presence of zinc or a similar metal generally in the form of an acid salt. Examples of sulfides of this type include 6,6'-dithiobis(5-methyl-4-nonene), 2-butenyl monosulfide and disulfide, and 2-methyl-2-butenyl monosulfide and disulfide.

The sulfurized olefins which are useful as a sulfur source include sulfurized olefins prepared by the reaction of an olefin (preferably containing 3 to 6 carbon atoms) or a lower molecular weight polyolefin derived therefrom, with a sulfur-containing compound such as sulfur, sulfur monochloride and/or sulfur dichloride, hydrogen sulfide, etc.

The sulfurized organic compounds may be sulfurized oils which may be prepared by treating natural or synthetic oils including mineral oils, lard oil, carboxylic acid esters derived from aliphatic alcohols and fatty acids or aliphatic carboxylic acids (e.g., myristyl oleate and oleyl oleate) sperm whale oil and synthetic sperm whale oil substitutes and synthetic unsaturated esters or glycerides. Stable sulfurized mineral lubricating oils can be obtained by heating a suitable mineral lubricating oil with from about 1 to about 5% of sulfur at a temperature above about 175° C. and preferably at about 200° to about 260° C. for several hours so as to obtain a reaction product which is substantially non-corrosive to copper. The mineral lubricating oils sulfurized in this manner may be distillate or residual oils obtained from paraffinic, naphthenic or mixed base crudes. Similarly, sulfurized fatty oils such as a sulfurized lard oil can be obtained by heating lard oil with about 10 to 15% of sulfur at a temperature of about 150° C. for a time sufficient to obtain a homogeneous product.

The sulfurized fatty acid esters useful as sulfur sources can be prepared by reacting sulfur, sulfur monochloride, and/or sulfur dichloride with an unsaturated fatty ester at elevated temperatures. Typical esters include $C_1$–$C_{20}$ alkyl esters of $C_8$–$C_{24}$ unsaturated fatty acids such as palmitoleic, oleic, ricinoleic, petroselic, vaccenic, linoleic, linolenic, oleostearic, licanic, etc. Sulfurized fatty acid esters prepared from mixed unsaturated fatty acid esters such as are obtained from animal fats and vegetable oils such as tall oil, linseed oil, olive oil, castor oil, peanut oil, rape oil, fish oil, sperm oil, etc also are useful. Specific examples of the fatty esters which can be sulfurized include lauryl tallate, methyl oleate, ethyl oleate, lauryl oleate, cetyl oleate, cetyl linoleate, lauryl ricinoleate, oleyl linoleate, oleyl stearate, and alkyl glycerides.

Another class of organic sulfur-containing compounds which can be used as a sulfur source compositions of the present invention includes sulfurized aliphatic esters of an olefinic monodicarboxylic acid. For example, aliphatic alcohols of from 1 to 30 carbon atoms can be used to esterify monocarboxylic acids such as acrylic acid, methacrylic acid, 2,4-pentadienic acid, etc. or fumaric acid, maleic acid, muconic acid, etc. Sulfurization of these esters is conducted with elemental sulfur, sulfur monochloride and/or sulfur dichloride.

Another class of sulfurized organic compounds are diestersulfides characterized by the following general formula $$-S_y[(CH_2)_xCOOR]_2$$

wherein x is from about 2 to about 5; y is from 1 to about 6, preferably 1 to about 3; and R is an alkyl group having from about 4 to about 20 carbon atoms. The R group may be a straight chain or branched chain group that is large enough to maintain the solubility of the compositions of the invention in oil. Typical diesters include the butyl, amyl, hexyl, heptyl, octyl, nonyl, decyl, tridecyl, myristyl, pentadecyl, cetyl, heptadecyl, stearyl, lauryl, and eicosyl diesters of thiodialkanoic acids such as propionic, butanoic, pentanoic and hexanoic acids. Of the diester sulfides, a specific example is dilauryl, 3,3'-thiodipropionate.

In one preferred embodiment, the sulfurized organic compound comprises sulfurized olefins. For example, organic polysulfides may be prepared by the sulfochlorination of olefins containing four or more carbon atoms and further treatment with inorganic higher polysulfides according to U.S. Pat. No. 2,708,199.

In one embodiment, sulfurized olefins are produced by (1) reacting sulfur monochloride with a stoichiometric excess of a low carbon atom olefin, (2) treating the resulting product with an alkali metal sulfide in the presence of free sulfur in a mole ratio of no less than 2:1 in an alcohol-water solvent, and (3) reacting that product with an inorganic base. This procedure is described in U.S. Pat. No. 3,471,404, and the disclosure of U.S.

Pat. No. 3,471,404 is hereby incorporated by reference for its discussion of this procedure for preparing sulfurized olefins and the sulfurized olefins thus produced. Generally, the olefin reactant contains from about 2 to 5 carbon atoms and examples include ethylene, propylene, butylene, isobutylene, amylene, etc. Briefly, in the first step, sulfur monochloride is reacted with from one to two moles of the olefin per mole of the sulfur monochloride, and the reaction is conducted by mixing the reactants at a temperature of from about 20° to 80° C. In the second step, the product of the first step is reacted with an alkali metal, preferably sodium sulfide, and sulfur. The mixture consists of up to about 2.2 moles of the metal sulfide per gram-atom of sulfur, and the mole ratio of alkali metal sulfide to the product of the first step is about 0.8 to about 1.2 moles of metal sulfide per mole of step (1) product. Generally, the second step is conducted in the presence of an alcohol or an alcohol-water solvent under reflux conditions. The third step of the process is the reaction between the phosphosulfurized olefin which contains from about 1 to about 3% of chlorine with an inorganic base in a water solution. Alkali metal hydroxide such as sodium hydroxide may be used. The reaction is continued until the chlorine content is reduced to below 0.5%, and this reaction is conducted at under reflux conditions for a period of from about 1 to 24 hours.

The sulfurized olefins which are useful in the compositions of the present invention also may be prepared by the reaction, under superatmospheric pressure, of olefinic compounds with a mixture of sulfur and hydrogen sulfide in the presence of a catalyst, followed by removal of low boiling materials. This procedure for preparing sulfurized compositions which are useful in the present invention is described in U.S. Pat. No. 4,191,659, the disclosure of which is hereby incorporated by reference for its description of the preparation of useful sulfurized compositions. An optional final step described in this patent is the removal of active sulfur by, for example, treatment with an alkali metal sulfide.

The olefinic compounds which may be sulfurized by this method and used as a sulfur source are diverse in nature. They contain at least one olefinic double bond, which is defined as a non-aromatic double bond; that is, one connecting two aliphatic carbon atoms. In its broadest sense, the olefin may be defined by the formula

$$R^1R^2C=CR^3R^4$$

wherein each of $R^1$, $R^2$, $R^3$ and $R^4$ is hydrogen or an organic group. In general, the R groups in the above formula which are not hydrogen may be satisfied by such groups as $-C(R^5)_3$, $-COOR^5$, $-CON(R^5)_2$, $-COON(R^5)_4$, $-COOM$, $-CN$, $-X$, $-YR^5$ or $-Ar$, wherein:

each $R^5$ is independently hydrogen, alkyl, alkenyl, aryl, substituted alkyl, substituted alkenyl or substituted aryl, with the proviso that any two $R^5$ groups can be alkylene or substituted alkylene whereby a ring of up to about 12 carbon atoms is formed;

M is one equivalent of a metal cation (preferably Group I or II, e.g., sodium, potassium, barium, calcium);

X is halogen (e.g., chloro, bromo, or iodo);

Y is oxygen or divalent sulfur;

Ar is an aryl or substituted aryl group of up to about 12 carbon atoms.

Any two of $R^1$, $R^2$, $R^3$ and $R^4$ may also together form an alkylene or substituted alkylene group; i.e., the olefinic compound may be alicyclic.

The natures of the substituents in the substituted moieties described above are not normally critical and any such substituent is useful so long as it is or can be made compatible with lubricating environments and does not interfere under the contemplated reaction conditions. Thus, substituted compounds which are so unstable as to deleteriously decompose under the reaction conditions employed are not contemplated. However, certain substituents such as keto or aldehydo can desirably undergo sulfurization. The selection of suitable substituents is within the skill of the art or may be established through routine testing. Typical of such substituents include any of the above-listed moieties as well as hydroxy, amidine, amino, sulfonyl, sulfinyl, sulfonate, nitro, phosphate, phosphite, alkali metal mercapto and the like.

The olefinic compound is usually one in which each R group which is not hydrogen is independently alkyl, alkenyl or aryl, or (less often) a corresponding substituted group. Monoolefinic and diolefinic compounds, particularly the former, are preferred, and especially terminal monoolefinic hydrocarbons; that is, those compounds in which $R^3$ and $R^4$ are hydrogen and $R^1$ and $R^2$ are alkyl or aryl, especially alkyl (that is, the olefin is aliphatic). Olefinic compounds having about 3 to about 30 and especially about 3 to 16 (most often less than 9) carbon atoms are particularly desirable.

Isobutene, propylene and their dimers, trimers and tetramers, and mixtures thereof are especially preferred olefinic compounds. Of these compounds, isobutylene and diisobutylene are particularly desirable because of their availability and the particularly high sulfur-containing compositions which can be prepared therefrom.

Commercial sources of sulfur and hydrogen sulfide are normally used for the purpose of this sulfurization reaction, and impurities normally associated therewith may be present without adverse results. Thus, commercial diisobutene is believed to contain essentially two isomeric forms and this mixture is contemplated for use according to the present invention.

The amounts of sulfur and hydrogen sulfide per mole of olefinic compound are, respectively, about 0.3–3.0 gram-atoms and about 0.1–1.5 moles. The preferred ranges are about 0.5–2.0 gram-atoms and about 0.4–1.25 moles respectively. In batch operations, the reactants are introduced at levels to provide these ranges. In semi-continuous and continuous operations, they may be admixed at any ratio but on a mass balance basis, they are present so as to be consumed in amounts within these ratios. Thus, for example, if the reaction vessel is initially charged with sulfur alone, the olefinic compound and hydrogen sulfide are added incrementally at a rate such that the desired ratio is obtained.

The temperature range in which the sulfurization reaction is carried out is generally about 50°–350° C. The preferred range is about 100°–200° C., with about 125°–180° C. being especially suitable. The reaction is conducted under superatmospheric pressure; this may be and usually is autogenous pressure (i.e., the pressure which naturally develops during the course of the reaction) but may also be externally applied pressure. The exact pressure developed during the reaction is dependent upon such factors as the design and operation of the system, the reaction temperature, and the vapor pressure of the reactants and products and it may vary during the course of the reaction.

It is frequently advantageous to incorporate materials useful as sulfurization catalysts in the reaction mixture. These materials may be acidic, basic or neutral. Useful neutral and acidic materials include acidified clays such as "Super Filtrol", p-toluenesulfonic acid, dialkylphosphorodithioic acids, and phosphorus sulfides such as phosphorus pentasulfide.

The preferred catalysts are basic materials. These may be inorganic oxides and salts such as sodium hydroxide, calcium oxide and sodium sulfide. The most desirable basic catalysts, however, are nitrogen bases including ammonia and amines. The amines include primary, secondary and tertiary hydrocarbyl amines wherein the hydrocarbyl groups are alkyl, aryl, aralkyl, alkaryl or the like and contain about 1–20 carbon atoms. Suitable amines include aniline, benzylamine, dibenzylamine, dodecylamine, morpholine, naphthylamine, tallow amines, N-ethyldipropylamine, N-phenylbenzylamine, N,N-diethylbutylamine, m-toluidine and 2,3-xylidine. Also useful are heterocyclic amines such as pyrrolidine, N-methylpyrrolidine, piperidine, pyridine and quinoline.

The amount of catalytic material used is generally about 0.05–2.0% of the weight of the olefinic compound. In the case of the preferred ammonia and amine catalysts, about 0.0005–0.5 mole per mole of olefin is preferred, and about 0.001–0.1 mole is especially desirable.

Also present in the reaction mixture may be water, either as a catalyst or as a diluent for one or more of the catalysts recited hereinabove. The amount of water, when present, is usually about 1–25% by weight of the olefinic compound. The presence of water is, however, not essential and when certain types of reaction equipment are used it may be advantageous to conduct the reaction under substantially anhydrous conditions.

The method is usually carried out in the absence of solvents and diluents other than water. However, it may sometimes be desirable to use a substantially inert, normally liquid organic diluent in the reaction. The nature of suitable diluents will readily be apparent to those skilled in the art.

The time required for the reaction to be completed will vary depending on the reagents, ratios thereof, the reaction temperature, the presence or absence of catalysts, and the purity of the reagents. The course of the reaction is conveniently followed by monitoring the pressure in the reaction vessel; the reaction can be considered complete when the pressure levels off to a constant value.

Following the preparation of the sulfurized mixture by the procedure described hereinabove, substantially all low boiling materials are removed. The nature of these low boiling materials will vary according to the amount and type of reactants used and the reaction conditions. It will also vary to some extent according to the use to which the sulfurized product is to be put, as well as such things as odor and flammability considerations, recycling needs of reactants and by-products, and the like. Most often, the product should have a flash point above about 30° C., preferably about 70° C. and desirably above about 100° C. as determined by ASTM Procedure D93. Reference is also made to ASTM Procedures D56 and D1310.

In addition to starting materials such as the olefinic compound, the low boiling materials will often include mercaptans and monosulfides, especially when the starting olefin contains less than 9 carbon atoms, and under these circumstances it is preferred that the product contain no more than about 5% by weight of such starting materials, mercaptans and monosulfides. If these materials are gaseous at ambient pressure and temperature, they may be removed in part simply by venting the reaction vessel, and they may be recycled if desired. In the case of less volatile starting materials, it may be necessary to resort to such techniques as distillation at atmospheric pressure or vacuum distillation or stripping. Another useful method is the passage of an inert gas such as nitrogen through the mixture of a suitable temperature and pressure. Large-scale gas chromatography and molecular distillation may also be useful.

Any solids present in the reaction mixture may be conveniently removed, in most instances, by merely pouring off the liquid product. If further removal of solids is desired, such conventional techniques as filtration or centrifugation may be used.

A further optional step in the method of this invention is the treatment of the sulfurized product, obtained as described hereinabove, to reduce active sulfur. By "active sulfur" is meant sulfur in a form which can cause staining of copper and similar materials. When active sulfur is to be reduced, any of several methods known in the art may be employed. An illustrative method is treatment with an alkali metal sulfide as described in U.S. Pat. No. 3,498,915.

Other optional treatments may be employed to improve such qualities as the odor, color and staining characteristics of the sulfurized compositions. These may include treatment with acidic clays such as Super Filtrol and filtration through fuller's earth, activated charcoal, alumina clays or the like. Such treatments are often not required when a basic catalyst is employed.

The exact chemical nature of the sulfurized compositions prepared in this manner is not known with certainty, and it is most convenient to describe them in terms of the method for their preparation. It appears, however, that when prepared from olefins containing less than 9 and particularly less than 7 carbon atoms, they comprise principally disulfides, trisulfides and tetrasulfides. The sulfur content of these sulfurized compositions is usually about 2–60% by weight, preferably about 25–60% and most desirably about 40–50%.

The method of preparing sulfurized olefins in this manner is illustrated by the following examples. Unless otherwise indicated in these and the other examples to follow, and in other parts of the specification and claims, all parts and percentages are by weight.

EXAMPLE S-1

Sulfur (526 parts, 16.4 moles) is charged to a jacketed, high-pressure reactor which is fitted with an agitator and internal cooling coils. Refrigerated brine is circulated through the coils to cool the reactor prior to the introduction of the gaseous reactants. After sealing the reactor, evacuating to about 2 torr and cooling, 920 parts (16.4 moles) of isobutene and 279 parts (8.2 moles) of hydrogen sulfide are charged to the reactor. The reactor is heated using steam in the external jacket, to a temperature of about 182° C. over about 1.5 hours. A maximum pressure of 1350 psig is reached at about 168° C. during this heat-up. Prior to reaching the peak reaction temperature, the pressure starts to decrease and continues to decrease steadily as the gaseous reactants are consumed. After about 10 hours at a reaction temperature of about 182° C., the pressure is 310-340 psig and the rate of pressure change is about 5-10 psig per hour. The unreacted hydrogen sulfide and isobutene are vented to a recovery system. After the pressure in the reactor has decreased to atmospheric, the sulfurized mixture is recovered as a liquid.

The mixture is blown with nitrogen at about 100° C. to remove low boiling materials including unreacted isobutene, mercaptans and monosulfides. The residue after nitrogen blowing is agitated with 5% Super Filtrol and filtered, using a diatomaceous earth filter aid. The filtrate is the desired sulfurized composition which contains 42.5% sulfur.

EXAMPLE S-2

Sulfur (151 parts) is charged to a reactor similar to the one described in Example I. The sulfur is heated to 160° C. and the reactor is sealed and evacuated. Hydrogen sulfide (72 parts) is added slowly to the reactor over a period of about 4.5 hours. Thereafter, 1.6 parts of the catalyst n-butylamine are added to the reactor after about 3.8 parts of hydrogen sulfide are added. Isobutylene (157 parts) is added slowly to the reactor containing the sulfur, catalyst, and about 10 parts of hydrogen sulfide in such a manner that the rates of addition of isobutylene and hydrogen sulfide are such as to maintain 10% molar excess of hydrogen sulfide until all the hydrogen sulfide is added. The addition of the remainder of isobutylene is continued until the entire 157 parts are added. The temperature is maintained in the range of between 160°-171° C. throughout the foregoing additions and reactions with occasional cooling being necessary. The reaction is held for 5 hours at 171° C., then unreacted hydrogen sulfide and isobutylene are vented to a recovery system until the pressure in the vessel is reduced to atmospheric. Separation of low boiling materials from the reaction crude is accomplished by nitrogen blowing, then vacuum stripping. The residue is then filtered. The filtrate is the desired sulfurized composition containing 47% sulfur by weight.

EXAMPLE S-3

Sulfur monochloride (2025 parts, 15.0 moles) is heated to 45° C. Through a sub-surface gas sparger, 1468 parts (26.2 moles of isobutylene gas) are fed into the reactor over a 5-hour period. The temperature is maintained between 45°-50° C. At the end of the sparging, the reaction mixture increases in weight of 1352 parts.

In a separate reaction vessel are added 2150 parts (16.5 moles) of 60% flake sodium sulfide, 240 parts (7.5 moles) sulfur, and a solution of 420 ml. of isopropanol in 4000 ml. of water. The contents are heated to 40° C. The adduct of the sulfur monochloride and isobutylene previously prepared is added over a three-quarter hour period while permitting the temperature to rise to 75° C. The reaction mixture is refluxed for 6 hours, and afterward the mixture is permitted to form into separate layers. The lower aqueous layer is discarded. The upper organic layer is mixed with two liters of 10% aqueous sodium hydroxide, and the mixture is refluxed for 6 hours. The organic layer is again removed and washed with one liter of water. The washed product is dried by heating at 90° C. and 30 mm. Hg. pressure for 30 minutes. The residue is filtered through diatomaceous earth filter aid to give 2070 parts of a clear yellow-orange liquid.

EXAMPLE S-4

Into a reactor is charged 102.8 parts of sulfur chloride under a nitrogen atmosphere which is maintained throughout the reaction, and about 718.5 parts of gaseous isobutylene are fed into the reactor through a submerged line. The isobutylene is added as rapidly as possible while maintaining the maximum batch temperature at about 49° C. with a cooling water bath. After all of the isobutylene is added, the bath temperature decreases indicating completion of the reaction.

In a separate vessel, a mixture of 340.3 parts of an 18% sodium sulfide solution and 363.8 parts of a 50% aqueous solution of sodium hydroxide is prepared and 128.77 parts of a 55.7% isopropyl alcohol and water mixture recovered from a previous batch are added. This addition is equivalent to 71 parts of dry isopropyl alcohol. The mixture is agitated, circulated and heated under reflux to a temperature of about 74° C. over a 2-hour period. While maintaining the batch temperature between about 75°-80° C., 168.13 parts of the isobutylene, sulfur chloride reaction product prepared above are added over a 5-hour period. The reaction mixture is maintained at about 80° C. and agitated for about 5 hours. The mixture then is cooled to about 38° C. and allowed to settle. The organic phase (138.7 parts) is separated from the aqueous phase and stripped of any remaining water and volatile materials. A filter aid is added to the residue with stirring, and the mixture then is filtered at about 50°-65° C. The filtrate is the desired product containing about 43% sulfur.

In another embodiment, the sulfurized organic compound is derived from a particular type of cyclic or bicyclic olefin which is a Diels-Alder adduct of at least one dienophile with at least one aliphatic conjugated diene. The sulfurized Diels-Alder adducts can be prepared by reacting various sulfurizing agents with the Diels-Alder adducts as described more fully below. Preferably, the sulfurizing agent is sulfur.

The Diels-Alder adducts are a well-known, art-recognized class of compounds prepared by the diene synthesis or Diels-Alder reaction. A summary of the prior art relating to this class of compounds is found in the Russian monograph, *Dienovyi Sintes*, Izdatelstwo Akademii Nauk SSSR, 1963 by A. S. Onischenko. (Translated into the English language by L. Mandel as A. S. Onischenko, *Diene Synthesis*, N. Y., Daniel Davey and Co., Inc., 1964. ) This monograph and references cited therein are incorporated by reference into the present specification.

The adducts and processes of preparing the adducts are further exemplified by the following examples.

EXAMPLE S-5

A mixture comprising 400 parts of toluene and 66.7 parts of aluminum chloride is charged to a two-liter flask fitted with a stirrer, nitrogen inlet tube, and a solid carbon dioxide-cooled reflux condenser. A second mixture comprising 640 parts (5 moles) of butyl acrylate and 240.8 parts of toluene is added to the AlCl$_3$ slurry while maintaining the temperature within the range of 37°-58° C. over a 0.25-hour period. Thereafter, 313 parts (5.8 moles) of butadiene is added to the slurry over a 2.75-hour period while maintaining the temperature of the reaction mass at 50°-61° C. by means of external cooling. The reaction mass is blown with nitrogen for about 0.33 hour and then transferred to a four-liter separatory funnel and washed with a solution of 150 parts of concentrated hydrochloric acid in 1100 parts of water. Thereafter, the product is subjected to two additional water washings using 1000 parts of water for each wash. The washed reaction product is subsequently distilled to remove unreacted butyl acrylate and toluene. The residue of this first distillation step is subjected to further distillation at a pressure of 9-10 millimeters of mercury whereupon 785 parts of the desired product is collected over the temperature of 105°-115° C.

EXAMPLE S-6

The adduct of isoprene and acrylonitrile is prepared by mixing 136 parts of isoprene, 106 parts of acrylonitrile, and 0.5 parts of hydroquinone (polymerization inhibitor) in a rocking autoclave and thereafter heating for 16 hours at a temperature within the range of 130°-140° C. The autoclave is vented and the contents decanted thereby producing 240 parts of a light yellow liquid. This liquid is stripped at a temperature of 90° C. and a pressure of 10 millimeters of mercury thereby yielding the desired liquid product as the residue.

EXAMPLE S-7

Using the procedure of Example S-6, 136 parts of isoprene, 172 parts of methyl acrylate, and 0.9 part of hydroquinone are converted to the isoprene methyl acrylate adduct.

EXAMPLE S-8

The general procedure of Example S-6 is repeated except that only 270 parts (5 moles) of butadiene is included in the reaction mixture.

The sulfur-containing compounds are readily prepared by heating a mixture of a sulfurizing agent such as sulfur, and at least one of the Diels-Alder adducts off the types discussed hereinabove at a temperature within the range of from about 110° C. to just below the decomposition temperature of the Diels-Alder adducts. Temperatures within the range of about 110° to about 200° C. will normally be used. This reaction results in a mixture of products, some of which have been identified. In the compounds of known structure, the sulfur reacts with the substituted, unsaturated, cycloaliphatic reactants at a double bond in the nucleus of the unsaturated reactant.

The molar ratio of sulfur to Diels-Alder adduct used in the preparation of the sulfur-containing composition is from about 0.5:1 to about 10:1 although the molar ratio generally will be less than about 4:1. In one embodiment of the invention, the molar ratio is less than about 1.7:1 and more preferably less than about 1:1.

The sulfurizing reaction can be conducted in the presence of suitable inert organic solvents such as mineral oils, alkanes of 7 to 18 carbons, etc., although no solvent is generally necessary. After completion of the reaction, the reaction mass can be filtered and/or subjected to other conventional purification techniques. There is no need to separate the various sulfur-containing products as they can be employed in the form of a reaction mixture comprising the compounds of known and unknown structure.

As hydrogen sulfide is an undesirable contaminent, it is advantageous to employ standard procedures for assisting in the removal of the H₂S from the products. Blowing with steam, alcohols, air, or nitrogen gas assists in the removal of H₂S as does heating at reduced pressures with or without the blowing.

It is sometimes advantageous to incorporate materials useful as sulfurization catalysts in the reaction mixture. These materials may be acidic, basic or neutral. Useful neutral and acidic materials include acidified clays such as "Super Filtrol", p-toluene sulfonic acid, dialkylphosphorodithioic acids, phosphorus sulfides such as phosphorus pentasulfide and phosphites such as triaryl phosphites (e.g., triphenyl phosphite).

The basic materials may be inorganic oxides and salts such as sodium hydroxide, calcium oxide and sodium sulfide. The most desirable basic catalysts, however, are nitrogen bases including ammonia and amines. The amines include primary, secondary and tertiary hydrocarbyl amines wherein the hydrocarbyl radicals are alkyl, aryl, aralkyl, alkaryl or the like and contain about 1-20 carbon atoms. Suitable amines include aniline, benzylamine, dibenzylamine, dodecylamine, naphthylamine, tallow amines, N-ethyldipropylamine, N-phenylbenzylamine, N,N-diethylbutylamine, m-toluidine and 2,3-xylidine. Also useful are heterocyclic amines such as pyrrolidine, N-methylpyrrolidine, piperidine, pyridine, morpholine and quinoline.

When a catalyst is used, the amount is generally about 0.05-2.0% of the weight of the adduct.

The following examples illustrate the preparation of the sulfur-containing compounds derived from Diels-Alder adducts.

EXAMPLE S-9

To 255 parts (1.65 moles) of the isoprenemethacrylate adduct of Example S-7 heated to a temperature of 110°-120° C., there are added 53 parts (1.65 moles) of sulfur flowers over a 45-minute period. The heating is continued for 4.5 hours at a temperature in the range of 130°-160° C. After cooling to room temperature, the reaction mixture is filtered through a medium sintered glass funnel. The filtrate consists of 301 parts of the desired sulfur-containing products.

EXAMPLE S-10

A reaction mixture comprising 1175 parts (6 moles) of the Diels-Alder adduct of butyl acrylate and isoprene and 192 parts (6 moles) of sulfur flowers is heated for 0.5 hour at 108°-110° C. and then to 155°-165° C. for 6 hours while bubbling nitrogen gas through the reaction mixture at 0.25 to 0.5 standard cubic feet per hour. At the end of the heating period, the reaction mixture is allowed to cool and filtered at room temperature. Thereafter, the product is permitted to stand for 24 hours and refiltered. The filtrate is the desired product.

EXAMPLE S-11

Sulfur (4.5 moles) and the adduct of isoprenemethyl methacrylate (4.5 moles) are mixed at room temperature and heated for one hour at 110° C. while blowing nitrogen through the reaction mass at 0.25-0.5 standard cubic feet per hour. Subsequently the reaction mixture is raised to a temperature of 150°-155° C. for 6 hours while maintaining the nitrogen blowing. After heating, the reaction mass is permitted to stand for several hours while cooling to room temperature and is thereafter filtered. The filtrate consists of 842 parts of the desired sulfur-containing product.

EXAMPLE S-12

A mixture of 1703 parts (9.4 moles) of a butyl acrylate-butadiene adduct prepared as in Example S-8, 280 parts (8.8 moles) of sulfur and 17 parts of triphenyl phosphite is prepared in a reaction vessel and heated gradually over 2 hours to a temperature of about 185° C. while stirring and sweeping with nitrogen. The reaction is exothermic near 160°–170° C., and the mixture is maintained at about 185° C. for 3 hours. The mixture is cooled to 90° C. over a period of 2 hours and filtered using a filter aid. The filtrate is the desired product containing 14.0% sulfur.

EXAMPLE S-13

The procedure of Example S-12 is repeated except that the triphenyl phosphite is omitted from the reaction mixture.

EXAMPLE S-14

The procedure of Example S-12 is repeated except that the triphenyl phosphite is replaced by 2.0 parts of triamyl amine as a sulfurization catalyst.

As previously mentioned, there is no need to separate the sulfur-containing products which are produced in the above reactions. The reaction product is a mixture which comprises the compounds whose structures have been ascertained but which also comprises compounds whose structures are unknown. Since it is economically unfeasible to separate the components of the reaction mixture, they are employed in combination as a mixture of sulfur-containing compounds.

The sulfur source may be at least one sulfurized terpene compound or a composition prepared by sulfurizing a mixture comprising at least one terpene and at least one other olefinic compound.

The term "terpene compound" as used herein is intended to include the various isomeric terpene hydrocarbons having the empirical formula $C_{10}H_{16}$, such as contained in turpentine, pine oil and dipentenes, and the various synthetic and naturally occuring oxygen-containing derivatives. Mixtures of these various compounds generally will be utilized, especially when natural products such as pine oil and turpentine are used. Pine oil, for example, which is obtained by destructive distillation of waste pine wood with super-heated steam comprises a mixture of terpene derivatives such as alpha-terpineol, beta-terpineol, alpha-fenchol, camphor, borneol/isoborneol, fenchone, estragole, dihydro alpha-terpineol, anethole, and other mono-terpene hydrocarbons. The specific ratios and amounts of the various components in a given pine oil will depend upon the particular source and the degree of purification. A group of pine oil-derived products are available commercially from Hercules Incorporated. It has been found that the pine oil products generally known as terpene alcohols available from Hercules Incorporated are particularly useful in the preparation of the sulfurized products used in the invention. Examples of such products include alpha-Terpineol containing about 95–97% of alpha-Terpineol, a high purity tertiary terpene alcohol mixture typically containing 96.3% of tertiary alcohols; Terpineol 318 Prime which is a mixture of isomeric terpineols obtained by dehydration of terpene hydrate and contains about 60–65 weight percent of alpha-terpineol and 15–20% beta-terpineol, and 18–20% of other tertiary terpene alcohols. Other mixtures and grades of useful pine oil products also are available from Hercules under such designations as Yarmor 302, Herco pine oil, Yarmor 302 W, Yarmor F and Yarmor 60.

The terpene compounds which can be utilized as the sulfur source may be sulfurized terpene compounds, sulfurized mixtures of terpene compounds or mixtures of at least one terpene compound and at least one sulfurized terpene compound. Sulfurized terpene compounds can be prepared by sulfurizing terpene compounds with sulfur, sulfur halides, or mixtures of sulfur or sulfur dioxide with hydrogen sulfide as will be described more fully hereinafter. Also, the sulfurization of various terpene compounds has been described in the prior art. For example, the sulfurization of pine oil is described in U.S. Pat. No. 2,012,446.

The other olefinic compound which may be combined with the terpene compound may be any of several olefinic compounds such as those described earlier. For example, the olefins may be of the type illustrated above.

The other olefin used in combination with the terpene also may be an unsaturated fatty acid, an unsaturated fatty acid ester, mixtures thereof, or mixtures thereof with the olefins described above. The term "fatty acid" as used herein refers to acids which may be obtained by hydrolysis of naturally occurring vegetable or animal fats or oils. These fatty acids usually contain from 16 to 20 carbon atoms and are mixtures of saturated and unsaturated fatty acids. The unsaturated fatty acids generally contained in the naturally occurring vegetable or animal fats and oils may contain one or more double bonds and such acids include palmitoleic acid, oleic acid, linoleic acid, linolenic acid, and erucic acid.

The unsaturated fatty acids may comprise mixtures of acids such as those obtained from naturally occurring animal and vegetable oils such as lard oil, tall oil, peanut oil, soybean oil, cottonseed oil, sunflower seed oil, or wheat germ oil. Tall oil is a mixture of rosin acids, mainly abietic acid, and unsaturated fatty acids, mainly oleic and linoleic acids. Tall oil is a by-product of the sulfate process for the manufacture of wood pulp.

It is frequently advantageous to incorporate materials useful as sulfurization promoters in the reaction mixture. These promoters which may be acidic, basic or neutral have been discussed earlier.

The amount of promoter material used is generally about 0.0005–2.0% of the combined weight of the terpene and olefinic compounds. In the case of the preferred ammonia and amine catalysts, about 0.0005–0.5 mole per mole of the combined weight is preferred, and about 0.001–0.1 mole is especially desirable.

Water is also present in the reaction mixture either as a promoter or as a diluent for one or more of the promoters recited hereinabove. The amount of water, when present, is usually about 1–25% by weight of the olefinic compound. The presence of water is, however, not essential and when certain types of reaction equipment are used it may be advantageous to conduct the reaction under substantially anhydrous conditions.

When promoters are incorporated into the reaction mixture as described hereinabove, it is generally observed is that the reaction can be conducted at lower temperatures, and the product generally is lighter in color.

The sulfurizing reagent used to sulfurize the terpenes may be, for example, sulfur, a sulfur halide such as sulfur monochloride or sulfur dichloride, a mixture of hydrogen sulfide and sulfur or sulfur dioxide, or the like. Sulfur, or mixtures of sulfur and hydrogen sulfide often are preferred. However, it will be understood that other sulfurization reagents may, when appropriate, be substituted therefor. Commercial sources of all the sulfurizing reagents are normally used for the purpose of this invention, and impurities normally associated with these commercial products may be present without adverse results.

When the sulfurization reaction is effected by the use of sulfur alone, the reaction is effected by merely heating the reagents with the sulfur at temperatures of from about 50° to 250° C., usually, from about 150° to about 210° C. The weight ratio of the combination of terpene and other olefin to sulfur is between about 5:1 and about 15:1, generally between about 5:1 and about 10:1. The sulfurization reaction is conducted with efficient agitation and generally in an inert atmosphere (e.g., nitrogen). If any of the components or reagents are appreciably volatile at the reaction temperature, the reaction vessel may be sealed and maintained under pressure. It is frequently advantageous to add the sulfur portionwise to the mixture of the other components.

When mixtures of sulfur and hydrogen sulfide are utilized in the process of the invention, the amounts of sulfur and hydrogen sulfide per mole of terpene and other olefin are, respectively, usually about 0.3 to about 3 grams-atoms and about 0.1 to about 1.5 moles. A preferred range is from about 0.5 to about 2.0 gram-atoms and about 0.4 to about 1.25 moles, respectively, and the most desirable ranges are about 0.8 to about 1.8 gram-atoms, and about 0.4 to about 0.8 mole, respectively. In batch operations, the components are introduced at levels to provide these ranges. In semi-continuous operations, they may be admixed at any ratio, but on a mass balance basis, they are present so as to be consumed in amounts within these ratios. Thus, for example, if the reaction vessel is initially charged with sulfur alone, the olefinic compound and hydrogen sulfide are added incrementally at a rate such that the desired ratio is obtained.

When mixtures of sulfur and hydrogen sulfide are utilized in the sulfurization reaction, the temperature range of the sulfurization reaction is generally from about 50° to about 350° C. The preferred range is about 100° to about 200° C. with about 120° to about 180° C. being especially suitable. The reaction often is conducted under super atmospheric pressure which may be and usually is autogenous pressure (i.e., pressure which naturally developed during the course of the reaction), but may also be externally applied pressure. The exact pressure developed during the reaction is dependent upon such factors as design and operation of the system, the reaction temperature, and the vapor pressure of the reactants and products, and it may vary during the course of the reaction.

While it is preferred generally that the reaction mixture consists entirely of the components and reagents described above, the reaction also may be carried out in the presence of an inert solvent (e.g., an alcohol, ether, ester, aliphatic hydrocarbon, halogenated aromatic hydrocarbon, etc.) which is liquid within the temperature range employed. When the reaction temperature is relatively high, for example, at about 200° C., there may be some evolution of sulfur from the product which is avoided when a lower reaction temperature such as from about 150°–170° C. is used.

The time required for the sulfurization reaction to be completed will vary depending upon the reagents, the ratios thereof, the reaction temperature, the presence or absence of promoters, and the purity of the reagents. When a mixture of sulfur and sulfur dioxide is used as the sulfurizing agent and the reaction is conducted at an elevated pressure in a closed vessel, the course of the reaction can be followed conveniently by monitoring the pressure in the reaction vessel. The reaction generally can be considered complete when the pressure levels off to a constant value. Following the preparation of the sulfurized mixture by the procedures described above, it is generally preferred to remove substantially all low boiling materials, typically by venting the reaction vessel or by distillation at atmospheric pressure, vacuum distillation or stripping, or the passage of an inert gas such as nitrogen through the mixture at a suitable temperature and pressure. Any solids which are present in the reaction mixture may be removed conveniently, in most instances, by merely pouring off the liquid product. If further removal of solids is desired, such conventional techniques as filtration or centrifugation may be used.

In some instances, it may be desirable to treat the sulfurized product obtained in accordance with the procedures described herein to reduce active sulfur.

The following examples illustrate the preparation of sulfurized terpene compounds and sulfurized mixtures of terpenes and olefinic compounds which are useful as a sulfurizing agent.

EXAMPLE S-15

To a reaction vessel that is charged 372 parts (2 equivalents) of a commercially available pine oil (Sargent Welch), and the pine oil is heated and stirred. Sulfur (128 parts) is added slowly with nitrogen blowing while the reaction temperature is maintained at about 35° C. After addition of the sulfur is completed, nitrogen is bubbled through the reaction mixture while it is heated to reflux at about 145° C. After a total reaction time of about 8 hours, the mixture is filtered through filter aid. The filtrate is the desired sulfurized product containing 23.35% sulfur (theory 25.6).

EXAMPLE S-16

The procedure of Example S-15 is repeated except that the reaction mixture comprises 186 parts of pine oil (1 equivalent) and 32 parts of sulfur (1.0 equivalent). The product obtained in this matter has a sulfur content of 15.6% (theory 14.68).

EXAMPLE S-17

To a reaction vessel is added 372 parts (2 equivalents) of pine oil and 96 parts (3 equivalents) of sulfur. When all of the sulfur is added, the mixture is heated to 150° C. with nitrogen blowing, and the mixture is maintained at this temperature for about 10 hours. The reaction mixture is filtered through a filter aid, and the filtrate is the desired product having a sulfur content of 17.25% (theory 20.5).

EXAMPLE S-18

A mixture of 186 parts (1 equivalent) of pine oil and 168 parts (1 equivalent) of polypropylene is prepared, and 96 parts (3 equivalents) of sulfur are added with stirring. The reaction mixture is heated to a temperature of about 170° C. with nitrogen blowing and maintained at this temperature for 10 hours. The reaction mixture then is cooled and filtered through filter aid. The filtrate is the desired product having a sulfur content of 16.79% (theory 21.33%).

The amines which are reacted with the phosphites in the presence of a sulfur source to form the amine salts may be ammonia, or a primary, secondary or tertiary amine, or mixtures thereof as represented by the formula $$R^3R^4R^5N$$

wherein $R^3$, $R^4$ and $R^5$ are each independently hydrogen, hydrocarbyl, aminohydrocarbyl hydroxyhydrocarbyl, aminohydrocarbyl or hydroxyhydrocarbyloxy hydrocarbyl groups, or $R^3$ and $R^4$ may be hydrocarbyl groups joined together to form a ring structure including the nitrogen atom and optionally additional heteroatoms such as nitrogen, oxygen, phosphorus or sulfur. Generally, the hydrocarbyl groups will contain up to about 150 carbon atoms and will more often be aliphatic hydrocarbyl groups containing from about 1 to about 30 carbon atoms.

In another embodiment the amine salt is derived from an acylated amine prepared by the reaction of a hydrocarbon-substituted carboxylic acid producing compound (e.g., a succinic acid producing compound) with at least about one-half of an equivalent, per equivalent of acid-producing compound, of an amine containing at least one hydrogen attached to a nitrogen atom. These acylated amines may be the same as the nitrogen-containing compositions described below as component (B) of the lubricant and functional fluid compositions of the invention.

In one preferred embodiment, the hydrocarbyl amines which are useful in preparing the borated amine salts of the present invention are primary hydrocarbyl amines containing from about 2 to about 30 carbon atoms in the hydrocarbyl group, and more preferably from about 4 to about 20 carbon atoms in the hydrocarbyl group. The hydrocarbyl group may be saturated or unsaturated. Representative examples of primary saturated amines are the lower alkyl amines such as methyl amine, ethyl amine, n-propyl amine, n-butyl amine, n-amyl amine, n-hexyl amine; those known as aliphatic primary fatty amines and commercially known as "Armeen" primary amines (products available from Armak Chemicals. Chicago, Ill.). Typical fatty amines include alkyl amines such as n-hexylamine, n-octylamine, n-decylamine, n-dodecylamine, n-tetradecylamine, n-pentadecylamine, n-hexadecylamine, n-octadecylamine (stearyl amine), etc. These Armeen primary amines are available in both distilled and technical grades. While the distilled grade will provide a purer reaction product, the desirable amides and imides will form in reactions with the amines of technical grade. Also suitable are mixed fatty amines such as Armak's Armeen-C, Armeen-O, Armeen-OL, Armeen-T, Armeen-HT, Armeen S and Armeen SD.

In another preferred embodiments, the borated amine salts of the composition of this invention are those derived from tertiary-aliphatic primary amines having at least about 4 carbon atoms in the alkyl group. For the most part, they are derived from alkyl amines having a total of less than about 30 carbon atoms in the alkyl group.

Usually the tertiary aliphatic primary amines are monoamines represented by the formula

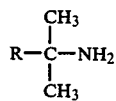

wherein R is a hydrocarbyl group containing from one to about 30 carbon atoms. Such amines are illustrated by tertiary-butyl amine, tertiary-hexyl primary amine, 1-methyl-1-amino-cyclohexane, tertiary-octyl primary amine, tertiary-decyl primary amine, tertiary-dodecyl primary amine, tertiary-tetradecyl primary amine, tertiary-hexadecyl primary amine, tertiary-octadecyl primary amine, tertiary-tetracosanyl primary amine, tertiary-octacosanyl primary amine.

Mixtures of amines are also useful for the purposes of this invention. Illustrative of amine mixtures of this type are "Primene 81R" which is a mixture of $C_{11}$–$C_{14}$ tertiary alkyl primary amines and "Primene JM-T" which is a similar mixture of $C_{18}$–$C_{22}$ tertiary alkyl primary amines (both are available from Rohm and Haas Company). The tertiary alkyl primary amines and methods for their preparation are well known to those of ordinary skill in the art and, therefore, further discussion is unnecessary. The tertiary alkyl primary amine useful for the purposes of this invention and methods for their preparation are described in U.S. Pat. No. 2,945,749 which is hereby incorporated by reference for its teaching in this regard.

Primary amines in which the hydrocarbon chain comprises olefinic unsaturation also are quite useful. Thus, the R' and R" groups may contain one or more olefinic unsaturations depending on the length of the chain, usually no more than one double bond per 10 carbon atoms. Representative amines are dodecenylamine, myristoleylamine, palmitoleylamine, oleylamine and linoleylamine. Such unsaturated amines also are available under the Armeen tradename.

Secondary amines include dialkylamines having two of the above alkyl groups including such commercial fatty secondary amines as Armeen 2C and Armeen HT, and also mixed dialkylamines where, for example, $R^1$ is a fatty amine and $R^2$ may be a lower alkyl group (1–9 carbon atoms) such as methyl, ethyl, n-propyl, i-propyl, butyl, etc., or $R^2$ may be an alkyl group bearing other non-reactive or polar substituents (CN, alkyl, carbalkoxy, amide, ether, thioether, halo, sulfoxide, sulfone) such that the essentially hydrocarbon character of the group is not destroyed. The fatty polyamine diamines include mono- or dialkyl, symmetrical or asymmetrical ethylene diamines, propane diamines (1,2, or 1,3), and polyamine analogs of the above. Suitable commercial fatty polyamines are "Duomeen C" (N-coco-1,3-diaminopropane), "Duomeen S" (N-soya-1,3-diaminopropane), "Duomeen T" (N-tallow-1,3-diaminopropane), or "Duomeen O" (N-oleyl-1,3-diaminopropane). "Duomeens" are commercially available diamines described in Product Data Bulletin No. 7-10R1 of Armak Chemical Co., Chicago, Ill. In another embodiment, the secondary amines may be cyclic amines such as piperidine, piperazine, morpholine, etc.

Other primary amines useful in the preparation of the amine salts (Ia) and (IIa) are the primary ether amines R"OR'NH$_2$ wherein R' is a divalent alkylene group having 2 to 6 carbon atoms and R" is a hydrocarbyl group of about 5 to about 150 carbon atoms. These primary ether amines are generally prepared by the reaction of an alcohol "R"OH with an unsaturated nitrile. The R" group of the alcohol can be a hydrocarbon-based group having up to about 150 carbon atoms. Typically, and for efficiency and economy, the alcohol is a linear or branched aliphatic alcohol with R" having up to about 50 carbon atoms, preferably up to 26 carbon atoms and most preferably R" has from 6 to 20 carbon atoms. The nitrile reactant can have from 2 to 6 carbon atoms with acrylonitrile being most preferred. Ether amines are known commercial products which are available under the name SURFAM ™ produced and marketed by Mars Chemical Company, Atlanta, Ga. Typical of such amines are those having from about 150 to about 400 molecular weight. Preferred etheramines are exemplified by those identified as SURFAM P14AB (branched $C_{14}$), SURFAM P16A (linear $C_{16}$), SURFAM P17AB (branched $C_{17}$). The carbon chain lengths (i.e., $C_{14}$, etc.) of the SURFAMS described above and used hereinafter are approximate and include the oxygen ether linkage. For example, a $C_{14}$ SURFAM would have the following general formula

The amines used to form the borated amine salts may be hydroxyhydrocarbyl amines. That is, $R^3$, $R^4$ and/or $R^5$ may be hydroxyhydrocarbyl or hydroxyhydrocarbyloxyhydrocarbyl groups. In one embodiment, these hydroxyhydrocarbyl amines can be represented by the formula

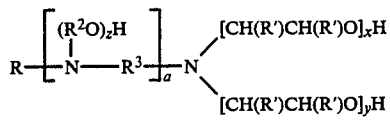

wherein R is a hydrocarbyl group generally containing from about 6 to about 30 carbon atoms, $R^2$ is an ethylene or propylene group, $R^3$ is an alkylene group containing up to about 5 carbon atoms, a is zero or one, each R' is hydrogen or a lower alkyl group, and x, y and z are each independently integers from zero to about 10, at least one of x, y and z being at least 1.

The above hydroxyhydrocarbyl amines can be prepared by techniques well known in the art, and many such hydroxyhydrocarbyl amines are commercially available. They may be prepared, for example, by reaction of primary amines containing at least 6 carbon atoms with various amounts of alkylene oxides such as ethylene oxide, propylene oxide, etc. The primary amines may be single amines or mixtures of amines such as obtained by the hydrolysis of fatty oils such as tallow oils, sperm oils, coconut oils, etc. Specific examples of fatty acid amines containing from about 6 to about 30 carbon atoms include saturated as well as unsaturated aliphatic amines such as octyl amine, decyl amine, lauryl amine, stearyl amine, oleyl amine, myristyl amine, palmityl amine, dodecyl amine, and octadecyl amine.

The useful hydroxyhydrocarbyl amines where a in the above formula is zero include 2-hydroxyethylhexylamine, 2-hydroxyethyloctylamine, 2-hydroxyethyldodecylamine, 2-hydroxyethyltetradecylamine, 2-hydroxyethylpentadecylamine, 2-hydroxyethyleicosylamine, 2-hydroxyethyltriacontylamine, 2-hydroxyethyloleylamine, 2-hydroxyethyltallowamine, 2-hydroxyethylsoyamine, bis-(2-hydroxyethyl)hexylamine, bis(2-hydroxyethyl)octylamine, bis(2-hydroxyethyl)dodecylamine, bis(2-hydroxyethyl)tetradecylamine, bis(2-hydroxyethyl)pentadecylamine, bis(2-hydroxyethyl)eicosylamine, bis(2-hydroxyethyl)triacontylamine, bis(2-hydroxyethyl)oleylamine, bis(2-hydroxyethyl)tallowamine, bis(2-hydroxyethyl)soyamine, 2-hydroxylpropyhexylamine, 2-hydroxypropyloctylamine, 2-hydroxypropyldodecylamine, 2-hydroxypropyltetradecylamine, 2-hydroxypropylpentadecylamine, 2-hydroxypropyleicosylamine, 2-hydroxypropyltriacontylamine, 2-hydroxypropyloleylamine, 2-hydroxypropyltallowamine, 2-hydroxypropylsoyamine, bis(2-hydroxypropyl)hexylamine, bis(2-hydroxypropyl)octylamine, bis(2-hydroxypropyl)dodecylamine, bis(2-hydroxypropyl)tetradecylamine, bis(2-hydroxypropyl)pentadecylamine, bis(2hydroxypropyl)eicosylamine, bis(2-hydroxypropyl)triacontylamine, bis(2-hydroxypropyl)oleylamine, bis(2-hydroxypropyl)tallowamine, bis(2-hydroxypropyl)soyamine and mixtures thereof. Also included are the comparable members wherein in the above formula at least one of x and y is at least 2, as for example, 2-hydroxyethoxyethylhexylamine.

A number of hydroxyhydrocarbyl amines wherein a is zero are available from the Armak Chemical Division of Akzona, Inc., Chicago, Ill., under the general trade designation "Ethomeen" and "Propomeen". Specific examples of such products include "Ethomeen C/15" which is an ethylene oxide condensate of a coconut fatty acid containing about 5 moles of ethylene oxide; "Ethomeen C/20" and "C/25" which also are ethylene oxide condensation products from coconut fatty acid containing about 10 and 15 moles of ethylene oxide respectively; "Ethomeen O/12" which is an ethylene oxide condensation product of oleyl amine containing about 2 moles of ethylene oxide per mole of amine. "Ethomeen S/15" and "S/20" which are ethylene oxide condensation products with stearyl amine containing about 5 and 10 moles of ethylene oxide per mole of amine respectively; and "Ethomeen T/12, T/15" and "T/25" which are ethylene oxide condensation products of tallow amine containing about 2, 5 and 15 moles of ethylene oxide per mole of amine respectively. "Propomeen O/12" is the condensation product of one mole of oleyl amine with 2 moles propylene oxide.

Commercially available examples of alkoxyalted amines where a is 1 include "Ethoduomeen T/13" and "T/20" which are ethylene oxide condensation products of N-tallow trimethylene diamine containing 3 and 10 moles of ethylene oxide per mole of diamine, respectively.

As mentioned above, the borated amine salts of the present invention generally are prepared by reacting at least one dihydrocarbyl phosphite, a sulfur source, at least one amine, and a boron compound. The boron compound may be included in the reaction mixture as such, or a borated amine salt can be prepared which is then added to the reaction mixture. In an alternative embodiment, the phosphite, sulfur source and boron compound can be reacted followed by the addition of the amine. The boron compounds which can be added to the reaction mixture are used to form the borated amine salts may be selected from the group consisting of boron trioxides, boron halides, boron acids, boron anhydrides, boron amides and esters of boron acids.

Organic solvents may be included in the reaction mixtures to facilitate handling. The organic solvents preferably should be selected from alcohols, ethers, aliphatic and aromatic hydrocarbons, and chlorinated saturated or unsaturated hydrocarbons. It is preferable that the reaction be conducted in a solvent in which the starting phosphite and the reaction product are soluble, and in which the sulfur source is insoluble.

The molar ratio of phosphite:sulfur source: amine:boron compound in the reaction mixture may vary over the ratio of about 1:0.4–1:0.4–1:0.5–5. Generally, about equimolar amounts of phosphite, sulfur source, amine are included in the reaction mixture although slightly less than one mole of sulfur is often used per mole of phosphite.

The reaction of the dihydrocarbyl phosphite, sulfur source, amine and boric acid can be conducted by heating the reaction mixture to a temperature up to the boiling point of the mixture. The reactions generally are conducted at atmospheric pressure at temperatures of up to about 100° C. for periods of about 3 to about 20 hours, although the reaction, depending upon the particular reactants, generally is completed in a period of from about 3 to about 10 hours. In some instances, the reaction is exothermic, and the exothermicity is moderated by the rate of addition of the various components to the reaction mixture. When the boron compound such as boric acid, is added to the reaction mixture as the last component, the reaction mixture is heated to an elevated temperature, generally under reduced pressure, and water is removed as it is formed in the reaction. At the end of the reaction, the reaction mixture can be filtered, and any solvent removed from the filtrate if desired.

The following examples illustrate the preparation of the borated amine salts of the present invention.

EXAMPLE A-1

A mixture of 291 parts (1.5 moles) of di-n-butyl phosphite and 48 parts (1.5 moles) of sulfur is prepared, and 525 parts (1.5 moles) of Ethomeen T/12 are added. The reaction is exothermic, and the temperature of the reaction mixture increases to about 70° C. The temperature of the reaction is controlled by the rate of addition of the Ethomeen T/12 which requires about 2.5 hours. After all of the Ethomeen T/12 is added, the reaction mixture is gradually heated to 150° C. and maintained at this temperature for about 3 hours. After cooling to room temperature, 100 parts of mineral oil and 93 parts of toluene are added as diluent to the reaction mixture followed by 62 parts (1 mole) of boric acid. The mixture is heated to about 110° C. to remove water of formation while purging with nitrogen. The reaction mixture is stripped to remove toluene, and filtered through a filter aid. The filtrate is the desired product containing 2.20% nitrogen (theory, 2.10), 4.74% phosphorus (theory, 4.65), 3.62% sulfur (theory, 4.80) and 1.34% boron (theory, 1.06).

EXAMPLE A-2

The general procedure of Example A-1 is repeated except that the mixture of di-n-butyl phosphite, sulfur and Ethomeen T/12 is heated to a temperature of 90°-95° C. for 3 hours. The product obtained in this manner contains 2.14% nitrogen (theory, 2.10), 4.70% phosphorus (theory 4.65), 4.95% sulfur (theory, 4.80) and 1.17% boron (theory, 1.06).

EXAMPLE A-3

A mixture of 402 parts (0.68 mole) of dioleyl phosphite and 222 parts (0.68 mole) of sulfur is prepared at room temperature and then heated to about 65°-70° C. whereupon 238 parts (0.68 mole) of Ethomeen T/12 are added in about 0.3 hour. A slight exothermic reaction occurs, and the mixture then is heated to 95°-100° C. and maintained at this temperature for 3 hours. After cooling overnight, 76 parts of mineral oil and 42 parts of toluene are added followed by the addition of 28 parts (0.457 mole) of boric acid. This reaction mixture is heated to 100° C. to remove water of formation while purging with nitrogen. The material is stripped to 100° C./5 mm. Hg. to remove toluene and then filtered through a filter aid. The filtrate is the desired product containing 1.19% nitrogen (theory, 1.26), 2.68% phosphorus (theory, 2.80), 3.60% sulfur (theory, 2.91) and 0.70% boron (theory, 0.65).

EXAMPLE A-4

A mixture of 466 parts (2.4 moles) of di-n-butyl phosphite and 828 parts (2.4 moles) of Ethomeen O/12 is prepared and heated to about 60° C. whereupon 77 parts (2.4 moles) of sulfur are added in small portions over a period of 0.5 hours. The reaction is exothermic, and the reaction temperature is controlled by the rate of addition of the sulfur. The temperature of the reaction mixture reaches 100° C. in 0.3 hour. After all of the sulfur is added, the reaction mixture is maintained at 90°-95° C. for 3 hours. The mixture then is cooled to about 80° C. whereupon 99 parts (1.6 moles) of boric acid are added in small portions over 0.3 hour. Toluene (250 parts) is added to the reaction flask at this stage, and water is removed from the reaction mixture as an azeotrope with toluene in 5 hours. The reaction mixture then is stripped to 120° C./10 mm. Hg. to remove residual toluene and filtered. The filtrate is the desired product containing 2.38% nitrogen (theory, 2.35), 5.49% phosphorus (theory, 5.22) and 1.31% boron (theory, 1.21).

EXAMPLE A-5

A mixture of 194 parts (1 mole) of di-n-butyl phosphite and 29 parts (0.9 mole) of sulfur is prepared at room temperature and then heated to 65°-70° C. whereupon 352 parts (1 mole) of a borated Ethomeen T/12 (containing 2.0% boron and 3.8% nitrogen) are added to the reaction mixture at 70°-90° C. over a period of 0.5 hour. The reaction is exothermic and the temperature is moderated by the rate of addition. The reaction mixture then is maintained at 90°-95° C. for 3 hours whereupon 57.5 parts of mineral oil diluent added to the reaction flask with agitation. The mixture then is filtered through a filter aid, and the filtrate is the desired product containing 10% mineral oil, 2.16% nitrogen (theory, 2.09), 4.79% phosphorus (theory, 4.85), 4.60% sulfur (theory, 4.53) and 1.10% boron (theory, 1.10).

EXAMPLE A-6

A mixture of 291 parts (1.5 mole) of di-n-butyl phosphite and 43.2 parts (1.35 moles) of sulfur is prepared at room temperature, and 525 parts (1.5 moles) of Ethomeen T/12 are added dropwise at about 70° C. over 2.5 hours. The reaction mixture then is heated to 95°-100° C. and maintained at this temperature for 3 hours. After cooling to room temperature, 99 parts of mineral oil diluent and 93 parts of toluene are added followed by the addition of 62 parts (1 mole) of boric acid. This mixture is heated to 100° C. to remove water or formation from the system while purging with nitrogen. After recovering about 27.5 parts of water in about 4.5 hours, the reaction mixture is stripped to remove toluene and then filtered through a filter aid. The filtrate is the desired product containing 2.07% nitrogen (theory, 2.11), 5.25% phosphorus (theory, 4.68), 4.38% sulfur (theory, 4.35) and 1.19% boron (theory 1.09).

EXAMPLE A-7

A mixture of 466 parts (2.4 moles) of di-n-butyl phosphite and 828 parts (2.4 moles) of Ethomeen O/12 is prepared and heated to about 60° C. whereupon 77 parts (2.4 moles) of sulfur are added in small amounts over 0.5 hour. The reaction is exothermic, and the exothermicity carries the reaction temperature up to about 135° C. over 0.3 hour. After cooling to 125°-130° C., the reaction mixture is maintained at this temperature for 3.5 hours whereupon the mixture is stripped at 125°-130° C./5 mm. Hg. The reaction mixture then is cooled to about 80° C., and 99 parts (1.6 moles) of boric acid are added to the reaction mixture over 0.3 hour followed by the addition of 250 parts of toluene. The reaction mixture is heated to remove water as an azeotrope with the toluene, and after about 45 parts of water is recovered, the remaining toluene is stripped under vacuum. The residue is filtered, and the filtrate is the desired product containing 2.40% nitrogen (theory, 2.35), 5.30% phosphorus (theory, 5.22), 5.56% sulfur (theory, 5.39) and 1.48% boron (theory, 1.21).

EXAMPLE A-8

A mixture of 97 parts (0.5 mole) of di-n-butyl phosphite and 13.6 parts (0.425 mole) of sulfur is prepared at room temperature and heated to 65°-70° C. whereupon 176 parts (0.5 mole) of a borated Ethomeen T/12 (containing 2.0% boron and 3.8% nitrogen) are added to the reaction mixture at 50°-95° C. over a period of 0.5 hour. The reaction is exothermic, and the exothermicity is moderated by the rate of addition. After all of the borated material is added, the reaction mixture is maintained at 90°-95° C. for 3 hours, and at the end of this heating period, 10% by weight of mineral oil is added, and the mixing is continued for 0.5 hour. The reaction mixture is filtered through a filter aid, and the filtrate is the desired product containing 2.09% nitrogen (theory, 2.10), 4.78% phosphorus (theory, 4.87), 4.22% sulfur (theory, 4.27) and 1.18% boron (theory, 1.10).

EXAMPLE A-9

The general procedure of Example A-8 is repeated except that the molar ratio of phosphite:sulfur:borated Ethomeen T/12 is 1:0.95:1. The product obtained in this manner contains 2.14% nitrogen (theory, 2.09), 4.73% phosphorus (theory, 4.84), 4.72% sulfur (theory, 4.75) and 1.15% boron (theory, 1.10).

EXAMPLE A-10

A di($C_{14-18}$alkyl) phosphite is prepared in accordance with the general procedure of Example P-1 by reacting 2 moles of Alfol 14-18 and 1 mole of dimethylphosphite. A mixture of 667 parts (1.25 moles) of the di($C_{14-18}$) phosphite, 244 parts (1.25 moles) of Primene 81-R and 40 parts (1.25 moles) of sulfur is prepared and heated gradually to 110° C. After cooling overnight, the reaction mixture is heated to 120° C. and maintained at this temperature for 1.5 hours. Boric acid (77.5 parts, 1.25 moles) is added over a period of 1 hour and the mixture is maintained at about 115° C. for 3 hours. The pressure is reduced to 15 mm. Hg. and the temperature maintained at 115°-120° C. for 1 hour and at 120° C./15 mm. Hg. for an additional 1.5 hours. The reaction mixture is cooled to 95° C. and filtered through a filter aid. The filtrate is the desired product containing 4.26% phosphorus (theory, 3.94), 4.15% sulfur (theory, 4.07), 1.77% nitrogen (theory, 1.78) and 1.56% boron (theory, 1.37).

EXAMPLE A-11

A mixture of 747 parts (1.4 moles) of the di-$C_{14-18}$ phosphite of Example A-10 and 44.8 parts (1.4 moles) of sulfur is prepared and heated to about 120° C. in a nitrogen atmosphere. The reaction mixture is maintained at 118°-123° C. for about 5 hours, and after cooling to about 60° C., 87 parts (1.4 moles) of boric acid and 200 parts of toluene are added. The temperature of the mixture is raised to 100° C. and maintained at this temperature for 3.5 hours. After cooling overnight, the mixture is heated to 100° C. and maintained at this temperature for about 14 hours and at 120° C. for 7.5 hours while removing a water-toluene azeotrope. The reaction mixture thereafter is stripped for 2 hours at 110°C./22 mm. Hg. and filtered through a filter aid. The filtrate is the desired borated intermediate. The filtrate is heated to about 40° C. whereupon 79.6 parts (0.408 mole) of Primene 81R are added over a period of 1.5 hours and thereafter at 100° C. for 2 hours. The product is filtered through a filter aid and the filtrate is the desired product containing 3.61% phosphorus (theory, 4.78), 4.28% sulfur (theory, 4.93), 0.91% nitrogen (theory, 0.97) and 0.845% boron (theory, 1.67).

EXAMPLE A-12

A mixture of 667 parts (1.25 moles) of the di-$C_{14-18}$ phosphite of Example A-10 and 40 parts (1.25 moles) of sulfur is prepared and heated to 120° C. The mixture is maintained at 120° C. for 4.5 hours while blowing with nitrogen. After cooling the mixture to about 105° C., 287 parts (1.25 moles) of tributylborate are added in 5 minutes. The reaction mixture is maintained at 105° C. for 1 hour and 20 minutes, and thereafter cooled overnight. The reaction mixture is heated to 105° C. and maintained at this temperature for 40 minutes, and thereafter the reaction mixture is stripped for 1 hour at 105° C./20 mm. Hg., followed by stripping at 105° C./15 mm. Hg. for 2.25 hours. Primene 81R (128 parts, 0.656 mole) is added slowly to the reaction mixture at about 95° C. After all of the Primene 81R is added, the reaction mixture is maintained at about 95° C. for about 1 hour and stripped at 95° C./15 mm. Hg. for 0.5 hour. The mixture is filtered through filter aid, and the filtrate is the desired product containing 3.48% phosphorus (theory, 3.76), 3.51% sulfur (theory, 3.89), 1.30% boron (theory, 1.31) and 0.88% nitrogen (theory, 0.89).

EXAMPLE A-13

A mixture of 667 parts (1.25 moles) of the di-$C_{14-18}$ phosphite of Example A-10 and 91 parts (1.25 moles) of n-butylamine is prepared and allowed to cool to about 34° C. Sulfur (40 parts, 1.25 moles) is added at this temperature and the reaction is exothermic up to about 55° C. When the exotherm subsides, the mixture is heated to 100° C. over a period of 0.5 hour and maintained at this temperature for 0.5 hour. The mixture is cooled overnight and is heated to 120°-145° C. to dissolve any remaining sulfur. After cooling, 26 parts (0.40 mole) of boric acid are added, and the mixture is heated to 80° C. and then at 110° C. for one hour at a reduced pressure of 30 mm. Hg. The temperature is raised to and maintained at 120° C. for 2.5 hours while water is removed. The pressure is reduced to about 22 mm. Hg. and the temperature maintained at 120° C. for 5.5 hours. The mixture is cooled to 70° C. and filtered through a filter aid. The filtrate is the desired product containing 4.55% phosphorus (theory, 4.84), 4.88% sulfur (theory, 5.00), 1.85% nitrogen (theory, 2.19) and 0.46% boron (theory, 0.54).

EXAMPLE A-14

An intermediate is prepared by reacting equimolar amounts of the di-$C_{14-18}$ phosphite of Example A-10, sulfur and Primene 81R. A mixture of 805 parts (1.06 moles) of this intermediate and 21.86 parts (0.352 mole) of boric acid is prepared, and 100 parts of toluene are added. The mixture is heated to 115° C. and maintained at this temperature for 2 hours. After cooling overnight, the mixture is heated to 120°–128° C. while removing water by distillation. After again cooling overnight, the mixture is stripped to 150° C. at 15 mm. Hg. for 1 hour. The mixture is cooled to 80° C. and filtered through a filter aid. The filtrate is the desired product containing 0.47% boron (theory, 0.47), 3.73% sulfur (theory, 4.23), 3.93% phosphorus (theory, 4.09) and 1.82% nitrogen (theory, 1.85).

The borated amine salts of monothiophosphoric acids such as described above may be utilized in a variety of applications including lubricating and functional fluid compositions and in aqueous systems. The lubricating compositions may be lubricating oils or greases.

Lubricant and functional fluid compositions containing the borated amine salts of the present invention generally will comprise a major amount of at least one oil of lubricating viscosity and a minor amount of the borated amine salts. The amount of borated amine salt in the lubricant or functional fluid more generally will be from about 0.1 to about 10% by weight. When utilized in aqueous systems, the aqueous systems will comprise at least about 40% of water and at least one of the borated amine salts described above.

OIL OF LUBRICATING VISCOSITY

The lubricating and oil-based functional fluid compositions of the present invention are based on diverse oils of lubricating viscosity, including natural and synthetic lubricating oils and mixtures thereof. These lubricating compositions containing the phosphorus-containing and nitrogen-containing compositions of the invention, are effective in a variety of applications including crankcase lubricating oils for spark-ignited and compression-ignited internal combustion engines, including automobile and truck engines, two-cycle engines, aviation piston engines, marine and low-load diesel engines, and the like. Also, automatic transmission fluids, transaxle lubricants, gear lubricants, metal-working lubricants, hydraulic fluids, and other lubricating oil and grease compositions can benefit from the incorporation of the compositions of this invention. The lubricating compositions are particularly effective as gear lubricants.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful. Synthetic lubricating oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of about 1000, diphenyl ether of polyethylene glycol having a molecular weight of about 500–1000, diethyl ether of polypropylene glycol having a molecular weight of about 1000–1500, etc.) or mono- and polycarboxylic esters thereof, for example, the acetic acid esters, mixed $C_3$–$C_8$ fatty acid esters, or the $C_{13}$Oxo acid diester of tetraethylene glycol.

Another suitable class of synthetic lubricating oils that can be used comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.) Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methylhexyl)silicate, tetra-(p-tert-butylphenyl)silicate, hexyl-(4-methyl-2-pentoxy)disiloxane, poly(methyl)siloxanes, poly(methylphenyl)siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the lubricants of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

(B) Soluble Nitrogen-Containing Compositions

In addition to the borated amine salts (A), the lubricating and functional fluid compositions of the present invention also may contain at least one soluble nitrogen-containing composition prepared by the reaction of a hydrocarbon-substituted succinic acid-producing compound (herein sometimes referred to as the "succinic acylating agent") with at least about one-half equivalent, per equivalent of acid-producing compound, of an amine containing at least one hydrogen attached to a nitrogen group. The nitrogen-containing compositions (B) obtained in this manner are usually complex mixtures whose precise composition is not readily identifiable. Thus, the compositions generally are described in terms of the method of preparation. The nitrogen-containing compositions are sometimes referred to herein as "acylated amines". The nitrogen-containing compositions (B) are either oil-soluble, or they are soluble in the oil-containing lubricating and functional fluids of this invention.

The soluble nitrogen-containing compositions useful as component (B) in the compositions of the present invention are known in the art and have been described in many U.S. patents including U.S. Pat. Nos. 3,172,892, 3,215,707, 3,272,746, 3,316,177, 3,341,542, 3,444,170, 3,454,607, 3,541,012, 3,630,904, 3,632,511, 3,787,374, 4,234,435. The above U.S. patents are expressly incorporated herein by reference for their teaching of the preparation of nitrogen-containing compositions useful as component (B).

In general, a convenient route for the preparation of the soluble nitrogen-containing compositions (B) comprises the reaction of a hydrocarbon-substituted succinic acid-producing compound ("carboxylic acid acylating agent") with an amine containing at least one hydrogen attached to a nitrogen atom (i.e., H—N=). The hydrocarbon-substituted succinic acid-producing compounds include the succinic acids, anhydrides, halides and esters. The number of carbon atoms in the hydrocarbon substituent on the succinic acid-producing compound may vary over a wide range provided that the nitrogen-containing composition (B) is soluble in the lubricating compositions of the present invention. Thus, the hydrocarbon substituent generally will contain an average of at least about 30 aliphatic carbon atoms and preferably will contain an average of at least about 50 aliphatic carbon atoms. In addition to the oil-solubility considerations, the lower limit on the average number of carbon atoms in the substituent also is based upon the effectiveness of such compounds in the lubricating oil compositions of the present invention. The hydrocarbyl substituent of the succinic compound may contain polar groups as indicated above, and, providing that the polar groups are not present in proportion sufficiently large to significantly alter the hydrocarbon character of the substituent.

The sources of the substantially hydrocarbon substituent include principally the high molecular weight substantially saturated petroleum fractions and substantially saturated olefin polymers, particularly polymers of mono-olefins having from 2 to 30 carbon atoms. The especially useful polymers are the polymers of 1-mono-olefins such as ethylene, propene, 1-butene, isobutene, 1-hexene, 1-octene, 2-methyl-1-heptene, 3-cyclohexyl-1-butene, and 2-methyl-5-propyl-1-hexene. Polymers of medial olefins, i.e., olefins in which the olefinic linkage is not at the terminal position, likewise are useful. They are illustrated by 2-butene, 2-pentene, and 4-octene.

Also useful are the interpolymers of the olefins such as those illustrated above with other interpolymerizable olefinic substances such as aromatic olefins, cyclic olefins, and polyolefins. Such interpolymers include, for example, those prepared by polymerizing isobutene with styrene; isobutene with butadiene; propene with isoprene; ethylene with piperylene; isobutene with chloroprene; isobutene with p-methyl styrene; 1-hexene with 1,3-hexadiene; 1-octene with 1-hexene; 1-heptene with 1-pentene; 3-methyl-1-butene with 1-octene; 3,3-dimethyl-1-pentene with 1-hexene; isobutene with styrene and piperylene; etc.

The relative proportions of the mono-olefins to the other monomers in the interpolymers influence the stability and oil-solubility of the final products derived from such interpolymers. Thus, for reasons of oil-solubility and stability the interpolymers contemplated for use in this invention should be substantially aliphatic and substantially saturated, i.e., they should contain at least about 80%, preferably at least about 95%, on a weight basis of units derived from the aliphatic mono-olefins and no more than about 5% of olefinic linkages based on the total number of carbon-to-carbon covalent linkages. In most instances, the percentage of olefinic linkages should be less than about 2% of the total number of carbon-to-carbon covalent linkages.

Specific examples of such interpolymers include copolymer of 95% (by weight) of isobutene with 5% of styrene; terpolymer of 98% of isobutene with 1% of piperylene and 1% of chloroprene; terpolymer of 95% of isobutene with 2% of 1-butene and 3% of 1-hexene, terpolymer of 80% of isobutene with 20% of 1-pentene and 20% of 1-octene; copolymer of 80% of 1-hexene and 20% of 1-heptene; terpolymer of 90% of isobutene with 2% of cyclohexene and 8% of propene; and copolymer of 80% of ethylene and 20% of propene.

Another source of the substantially hydrocarbon group comprises saturated aliphatic hydrocarbons such as highly refined high molecular weight white oils or synthetic alkanes such as are obtained by hydrogenation of high molecular weight olefin polymers illustrated above or high molecular weight olefinic substances.

The use of olefin polymers having molecular weights (Mn) of about 700–10,000 is preferred. Higher molecular weight olefin polymers having molecular weights (Mn) from about 10,000 to about 100,000 or higher have been found to impart also viscosity index improving properties to the final products of this invention. The use of such higher molecular weight olefin polymers often is desirable. Preferably the substituent is derived from a polyolefin characterized by an Mn value of about 700 to about 10,000, and an Mw/Mn value of 1.0 to about 4.0.

In preparing the substituted succinic acylating agents of this invention, one or more of the above-described polyalkenes is reacted with one or more acidic reactants selected from the group consisting of maleic or fumaric reactants such as acids or anhydrides. Ordinarily the maleic or fumaric reactants will be maleic acid, fumaric acid, maleic anhydride, or a mixture of two or more of these. The maleic reactants are usually preferred over the fumaric reactants because the former are more readily available and are, in general, more readily reacted with the polyalkenes (or derivatives thereof) to prepare the substituted succinic acid-producing compounds useful in the present invention. The especially preferred reactants are maleic acid, maleic anhydride, and mixtures of these. Due to availability and ease of reaction, maleic anhydride will usually be employed.

For convenience and brevity, the term "maleic reactant" is often used hereinafter. When used, it should be understood that the term is generic to acidic reactants selected from maleic and fumaric reactants including a mixture of such reactants. Also, the term "succinic acylating agents" is used herein to represent the substituted succinic acid-producing compounds.

One procedure for preparing the substituted succinic acylating agents of this invention is illustrated, in part, in U.S. Pat. No. 3,219,666 which is expressly incorporated herein by reference for its teachings in regard to preparing succinic acylating agents. This procedure is conveniently designated as the "two-step procedure". It involves first chlorinating the polyalkene until there is an average of at least about one chloro group for each molecular weight of polyalkene. (For purposes of this invention, the molecular weight of the polyalkene is the weight corresponding to the Mn value.) Chlorination involves merely contacting the polyalkene with chlorine gas until the desired amount of chlorine is incorporated into the chlorinated polyalkene. Chlorination is generally carried out at a temperature of about 75° C. to about 125° C. If a diluent is used in the chlorination procedure, it should be one which is not itself readily subject to further chlorination. Poly- and perchlorinated and/or fluorinated alkanes and benzenes are examples of suitable diluents.

The second step in the two-step chlorination procedure, for purposes of this invention, is to react the chlorinated polyalkene with the maleic reactant at a temperature usually within the range of about 100° C. to about 200° C. The mole ratio of chlorinated polyalkene to maleic reactant is usually about 1:1. (For purposes of this invention, a mole of chlorinated polyalkene is that weight of chlorinated polyalkene corresponding to the Mn value of the unchlorinated polyalkene.) However, a stoichiometric excess of maleic reactant can be used, for example, a mole ratio of 1:2. If an average of more than about one chloro group per molecule of polyalkene is introduced during the chlorination step, then more than one mole of maleic reactant can react per molecule of chlorinated polyalkene. Because of such situations, it is better to describe the ratio of chlorinated polyalkene to maleic reactant in terms of equivalents. (An equivalent weight of chlorinated polyalkene, for purposes of this invention, is the weight corresponding to the Mn value divided by the average number of chloro groups per molecule of chlorinated polyalkene while the equivalent weight of a maleic reactant is its molecular weight.) Thus, the ratio of chlorinated polyalkene to maleic reactant will normally be such as to provide about one equivalent of maleic reactant for each mole of chlorinated polyalkene up to about one equivalent of maleic reactant for each equivalent of chlorinated polyalkene with the understanding that it is normally desirable to provide an excess of maleic reactant; for example, an excess of about 5% to about 25% by weight. Unreacted excess maleic reactant may be stripped from the reaction product, usually under vacuum, or reacted during a further stage of the process as explained below.

The resulting polyalkene-substituted succinic acylating agent is, optionally, again chlorinated if the desired number of succinic groups are not present in the product. If there is present, at the time of this subsequent chlorination, any excess maleic reactant from the second step, the excess will react as additional chlorine is introduced during the subsequent chlorination. Otherwise, additional maleic reactant is introduced during and/or subsequent to the additional chlorination step. This technique can be repeated until the total number of succinic groups per equivalent weight of substituent groups reaches the desired level.

Another procedure for preparing substituted succinic acid acylating agents of the invention utilizes a process described in U.S. Pat. No. 3,912,764 and U.K. Pat. No. 1,440,219, both of which are expressly incorporated herein by reference for their teachings in regard to that process. According to that process, the polyalkene and the maleic reactant are first reacted by heating them together in a "direct alkylation" procedure. When the direct alkylation step is completed, chlorine is introduced into the reaction mixture to promote reaction of the remaining unreacted maleic reactants. According to the patents, 0.3 to 2 or more moles of maleic anhydride are used in the reaction for each mole of olefin polymer; i.e., polyalkylene. The direct alkylation step is conducted at temperatures of 180°–250° C. During the chlorine-introducing stage, a temperature of 160°–225° C. is employed. In utilizing this process to prepare the substituted succinic acylating agents of this invention, it would be necessary to use sufficient maleic reactant and chlorine to incorporate at least 1.3 succinic groups into the final product for each equivalent weight of polyalkene.

Another process for preparing the substituted succinic acylating agents used in this invention is the so-called "one-step" process. This process is described in U.S. Pat. Nos. 3,215,707 and 3,231,587. Both are expressly incorporated herein by reference for their teachings in regard to that process.

Basically, the one-step process involves preparing a mixture of the polyalkene and the maleic reactant containing the necessary amounts of both to provide the desired substituted succinic acylating agents of this invention. This means that there must be at least one mole of maleic reactant for each mole of polyalkene in order that there can be at least one succinic group for each equivalent weight of substituent groups. Chlorine is then introduced into the mixture, usually by passing chlorine gas through the mixture with agitation, while maintaining a temperature of at least about 140° C.

A variation of this process involves adding additional maleic reactant during or subsequent to the chlorine introduction but, for reasons explained in U.S. Pat. Nos. 3,215,707 and 3,231,587, this variation is presently not as preferred as the situation where all the polyalkene and all the maleic reactant are first mixed before the introduction of chlorine.

Usually, where the polyalkene is sufficiently fluid at 140° C. and above, there is no need to utilize an additional substantially inert, normally liquid solvent/diluent in the one-step process. However, as explained hereinbefore, if a solvent/diluent is employed, it is preferably one that resists chlorination. Again, the poly- and perchlorinated and/or -fluorinated alkanes, cycloalkanes, and benzenes can be used for this purpose.

Chlorine may be introduced continuously or intermittently during the one-step process. The rate of introduction of the chlorine is not critical although, for maximum utilization of the chlorine, the rate should be about the same as the rate of consumption of chlorine in the course of the reaction. When the introduction rate of chlorine exceeds the rate of consumption, chlorine is evolved from the reaction mixture. It is often advantageous to use a closed system, including superatmospheric pressure, in order to prevent loss of chlorine so as to maximize chlorine utilization.

The minimum temperature at which the reaction in the one-step process takes place at a reasonable rate is about 140° C. Thus, the minimum temperature at which the process is normally carried out is in the neighborhood of 140° C. The preferred temperature range is usually between about 160°–220° C. Higher temperatures such as 250° C. or even higher may be used but usually with little advantage. In fact, temperatures in excess of 220° C. are often disadvantageous with respect to preparing the particular acylated succinic compositions of this invention because they tend to "crack" the polyalkenes (that is, reduce their molecular weight by thermal degradation) and/or decompose the maleic reactant. For this reason, maximum temperatures of about 200°–210° C. are normally not exceeded. The upper limit of the useful temperature in the one-step process is determined primarily by the decomposition point of the components in the reaction mixture including the reactants and the desired products. The decomposition point is that temperature at which there is sufficient decomposition of any reactant or product such as to interfere with the production of the desired products.

In the one step process, the molar ratio of maleic reactant to chlorine is such that there is at least about one mole of chlorine for each mole of maleic reactant to be incorporated into the product. Moreover, for practical reasons, a slight excess, usually in the neighborhood of about 5% to about 30% by weight of chlorine, is utilized in order to offset any loss of chlorine from the reaction mixture. Larger amounts of excess chlorine may be used but do not appear to produce any beneficial results.

The molar ratio of polyalkene to maleic reactant preferably is such that there is at last about one mole of maleic reactant for each mole of polyalkene. This is necessary in order that there can be at least 1.0 succinic group per equivalent weight of substituent group in the product. Preferably, however, an excess of maleic reactant is used. Thus, ordinarily about a 5% to about 25% excess of maleic reactant will be used relative to that amount necessary to provide the desired number of succinic groups in the product.

The amines which are reacted with the succinic acid-producing compounds to form the nitrogen-containing compositions (B) may be monoamines and polyamines. The monoamines and polyamines must be characterized by the presence within their structure of at least one H—H< group. Therefore, they have at least one primary (i.e., H$_2$N—) or secondary amino (i.e., 1 H—N=) group. The amines can be aliphatic, cycloaliphatic, aromatic, or heterocyclic, including aliphatic-substituted cycloaliphatic, aliphatic-substituted aromatic, aliphatic-substituted heterocyclic, cycloaliphatic-substituted aliphatic, cycloaliphatic-substituted aromatic, cycloaliphatic-substituted heterocyclic, aromatic-substituted aliphatic, aromatic-substituted cycloaliphatic, aromatic-subtituted heterocyclic-substituted alicyclic, and heterocyclic-substituted aromatic amines and may be saturated or unsaturated. The amines may also contain non-hydrocarbon substituents or groups as long as these groups do not significantly interfere with the reaction of the amines with the acylating reagents of this invention. Such non-hydrocarbon substituents or groups include lower alkoxy, lower alkyl mercapto, nitro, interrupting groups such as —O— and —S— (e.g., as in such groups as —CH$_2$CH$_2$—X—CH$_2$CH$_2$— where X is —O— or —S—). In general, the amine of (B) may be characterized by the formula $$R_1R_2NH$$

wherein $R_1$ and $R_2$ are each independently hydrogen or hydrocarbon, amino-substituted hydrocarbon, hydroxy-substituted hydrocarbon, alkoxy-substituted hydrocarbon, amino, carbamyl, thiocarbamyl, guanyl and acylimidoyl groups provided that only one of $R_1$ and $R_2$ may be hydrogen.

With the exception of the branched polyalkylene polyamine, the polyoxyalkylene polyamines, and the high molecular weight hydrocarbyl-substituted amines described more fully hereafter, the amines ordinarily contain less than about 40 carbon atoms in total and usually not more than about 20 carbon atoms in total.

Aliphatic monoamines include mono-aliphatic and di-aliphatic substituted amines wherein the aliphatic groups can be saturated or unsaturated and straight or branched chain. Thus, they are primary or secondary aliphatic amines. Such amines include, for example, mono- and di-alkyl-substituted amines, mono- and dialkenyl-substituted amines, and amines having one N-alkenyl substituent and one N-alkyl substituent and the like. The total number of carbon atoms in these aliphatic monoamines will, as mentioned before, normally not exceed about 40 and usually not exceed about 20 carbon atoms. Specific examples of such monoamines include ethylamine, diethylamine, n-butylamine, di-n-butylamine, allylamine, isobutylamine, cocoamine, stearylamine, laurylamine, methyllaurylamine, oleylamine, N-methyl-octylamine, dodecylamine, octadecylamine, and the like. Examples of cycloaliphatic-substituted aliphatic amines, aromatic-substituted aliphatic amines, and heterocyclic-substituted aliphatic amines, include 2-(cyclohexyl)-ethylamine, benzylamine, phenethylamine, and 3-(furylpropyl)amine.

Cycloaliphatic monoamines are those monoamines wherein there is one cycloaliphatic substituent attached directly to the amino nitrogen through a carbon atom in the cyclic ring structure. Examples of cycloaliphatic monoamines include cyclohexylamines, cyclopentylamines, cyclohexenylamines, cyclopentenylamines, N-ethyl-cyclohexylamine, dicyclohexylamines, and the like. Examples of aliphatic-substituted, aromatic-substituted, and heterocyclic-substituted cycloaliphatic monoamines include propyl-substituted cyclohexylamines, phenyl-substituted cyclopentylamines, and pyranyl-substituted cyclohexylamine.

Aromatic amines suitable as (a) include those monoamines wherein a carbon atom of the aromatic ring structure is attached directly to the amino nitrogen. The aromatic ring will usually be a mononuclear aromatic ring (i.e., one derived from benzene) but can include fused aromatic rings, especially those derived from naphthalene. Examples of aromatic monoamines include aniline, di(para-methylphenyl)amine, naphthylamine, N-(n-butyl)aniline, and the like. Examples of aliphatic-substituted, cycloaliphatic-substituted, and heterocyclic-substituted aromatic monoamines are para-ethoxyaniline, para-dodecylaniline, cyclohexyl-substituted naphthylamine, and thienyl-substituted aniline.

The polyamines from which (B) is derived include principally alkylene amines conforming for the most part to the formula

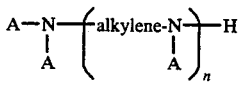

wherein n is an integer preferably less than about 10, A is a hydrogen group or a substantially hydrocarbon group preferably having up to about 30 carbon atoms, and the alkylene group is preferably a lower alkylene group having less than about 8 carbon atoms. The alkylene amines include principally methylene amines, ethylene amines, butylene amines, propylene amines, pentylene amines, hexylene amines, heptylene amines, octylene amines, other polymethylene amines. They are exemplified specifically by: ethylene diamine, triethylene tetramine, propylene diamine, decamethylene diamine, octamethylene diamine, di(heptamethylene) triamine, tripropylene tetramine, tetraethylene pentamine, trimethylene diamine, pentaethylene hexamine, di(-trimethylene) triamine. Higher homologues such as are obtained by condensing two or more of the above-illustrated alkylene amines likewise are useful.

The ethylene amines are especially useful. They are described in some detail under the heading "Ethylene Amines" in Encyclopedia of Chemical Technology, Kirk and Othmer, Vol. 5, pp. 898–905, Interscience Publishers, New York (1950). Such compounds are prepared most conveniently by the reaction of an alkylene chloride with ammonia. The reaction results in the production of somewhat complex mixtures of alkylene amines, including cyclic condensation products such as piperazines. These mixtures find use in the process of this invention. On the other hand, quite satisfactory products may be obtained also by the use of pure alkylene amines. An especially useful alkylene amine for reasons of economy as well as effectiveness of the products derived therefrom is a mixture of ethylene amines prepared by the reaction of ethylene chloride and ammonia and having a composition which corresponds to that of tetraethylene pentamine.

Hydroxyalkyl-substituted alkylene amines, i.e., alkylene amines having one or more hydroxyalkyl substituents on the nitrogen atoms, likewise are contemplated for use herein. The hydroxyalkyl-substituted alkylene amines are preferably those in which the alkyl group is a lower alkyl group, i.e., having less than about 6 carbon atoms. Examples of such amines include N-(2-hydroxyethyl)ethylene diamine, N,N'-bis(2-hydroxyethyl)ethylene diamine, 1-(2-hydroxyethyl)piperazine, monohydroxypropyl-substituted diethylene triamine, 1,4-bis(2-hydroxypropyl)piperazine, di-hydroxypropyl-substituted tetraethylene pentamine, N-(3-hydroxypropyl)tetramethylene diamine, and 2-heptadecyl-1-(2-hydroxyethyl)imidazoline.

Higher homologues such as are obtained by condensation of the above illustrated alkylene amines or hydroxy alkyl-substituted alkylene amines through amino radicals or through hydroxy radicals are likewise useful. It will be appreciated that condensation through amino radicals results in a higher amine accompanied with removal of ammonia and that condensation through the hydroxy radicals results in products containing ether linkages accompanied with removal of water.

Heterocyclic mono- and polyamines can also be used in making the nitrogen-containing compositions (B). As used herein, the terminology "heterocyclic mono- and polyamine(s)" is intended to describe those heterocyclic amines containing at least one primary or secondary amino group and at least one nitrogen as a heteroatom in the heterocyclic ring. However, as long as there is present in the heterocyclic mono- and polyamines at least one primary or secondary amino group, the hetero-N atom in the ring can be a tertiary amino nitrogen; that is, one that does not have hydrogen attached directly to the ring nitrogen. Heterocyclic amines can be saturated or unsaturated and can contain various substituents such as nitro, alkoxy, alkyl mercapto, alkyl, alkenyl, aryl, alkaryl, or aralkyl substituents. Generally, the total number of carbon atoms in the substituents will not exceed about 20. Heterocyclic amines can contain hetero atoms other than nitrogen, especially oxygen and sulfur. Obviously they can contain more than one nitrogen hetero atom. The 5- and 6-membered heterocyclic rings are preferred.

Among the suitable heterocyclics are aziridines, azetidines, azolidines, tetra- and di-hydro pyridines, pyrroles, indoles, piperidines, imidazoles, di- and tetrahydroimidazoles, piperazines, isoindoles, purines, morpholines, thiomorpholines, N-aminoalkylmorpholines, N-aminoalkylthiomorpholines, N-aminoalkylpiperazines, N,N'-di-aminoalkylpiperazines, azepines, azocines, azonines, azecines and tetra-, di- and perhydro derivatives of each of the above and mixtures of two or more of these heterocyclic amines. Preferred heterocyclic amines are the saturated 5- and 6-membered heterocyclic amines containing only nitrogen, oxygen and/or sulfur in the hetero ring, especially the piperidines, piperazines, thiomorpholines, morpholines, pyrrolidines, and the like. Piperidine, aminoalkylsubstituted piperidines, piperazine, aminoalkylsubstituted piperazines, morpholine, aminoalkylsubstituted morpholines, pyrrolidine, and aminoalkylsubstituted pyrrolidines, are especially preferred. Usually the aminoalkyl substituents are substituted on a nitrogen atom forming part of the hetero ring. Specific examples of such heterocyclic amines include N-aminopropylmorpholine, N-aminoethylpiperazine, and N,N'-diaminoethylpiperazine.

The nitrogen-containing composition (B) obtained by reaction of the succinic acid-producing compounds and the amines described above may be amine salts, amides, imides, imidazolines as well as mixtures thereof. To prepare the nitrogen-containing composition (B), one or more of the succinic acid-producing compounds and one or more of the amines are heated, optionally in the presence of a normally liquid, substantially inert organic liquid solvent/diluent at an elevated temperature generally in the range of from about 80° C. up to the decomposition point of the mixture or the product. Normally, temperatures in the range of about 100° C. up to about 300° C. are utilized provided that 300° C. does not exceed the decomposition point.

The succinic acid-producing compound and the amine are reacted in amounts sufficient to provide at least about one-half equivalent, per equivalent of acid-producing compound, of the amine. Generally, the maximum amount of amine present will be about 2 moles of amine per equivalent of succinic acid-producing compound. For the purposes of this invention, an equivalent of the amine is that amount of the amine corresponding to the total weight of amine divided by the total number of nitrogen atoms present. Thus, octyl amine has an equivalent weight equal to its molecular weight; ethylene diamine has an equivalent weight equal to one-half its molecular weight; and aminoethyl piperazine has an equivalent weight equal to one-third its molecular weight. The number of equivalents of succinic acid-producing compound depends on the number of carboxylic functions present in the hydrocarbon-substituted succinic acid-producing compound. Thus, the number of equivalents of hydrocarbon-substituted succinic acid-producing compound will vary with the number of succinic groups present therein, and generally, there are two equivalents of acylating reagent for each succinic group in the acylating reagents. Conventional techniques may be used to determine the number of carboxyl functions (e.g., acid number, saponification number) and, thus, the number of equivalents of acylating reagent available to react with amine. Additional details and examples of the procedures for preparing the nitrogen-containing compositions useful in the present invention by reaction of succinic acid-producing compounds and amines are included in, for example, U.S. Pat. Nos. 3,172,892; 3,219,666; 3,272,746; and 4,234,435, the disclosures of which are hereby incorporated by reference.

The nitrogen-containing composition (B) useful in the lubricating compositions of the present invention may also contain boron. The nitrogen- and boron-containing compositions are prepared by the reaction of (B-1) at least one boron compound selected from the class consisting of boron trioxides, boron halides, boron acids, boron amides and esters of boron acids with (B-2) at least one soluble acylated nitrogen intermediate prepared by the reaction of a hydrocarbon substituted succinic acid-producing compound (acylating agent) with at least about one-half equivalent, per equivalent of acid-producing compound, of an amine containing at least one hydrogen attached to a nitrogen atom.

The acylated nitrogen intermediate (B-2) described above is identical to the oil-soluble nitrogen-containing compositions (B) described above which have not been reacted with a boron compound. The amount of boron compound reacted with the oil-soluble acylated nitrogen intermediate (B-2) generally is sufficient to provide from about 0.1 atomic proportion of boron for each mole of the acylated nitrogen composition up to about 10 atomic proportions of boron for each atomic proportion of nitrogen of said acylated nitrogen composition. More generally the amount of boron compound present is sufficient to provide from about 0.5 atomic proportion of boron for each mole of the acylated nitrogen composition to about 2 atomic proportions of boron for each atomic proportion of nitrogen used.

The boron compounds useful in the above reaction include boron oxide, boron oxide hydrate, boron trioxide, boron trifluoride, boron tribromide, boron trichloride, boron acids such as boronic acid (i.e., alkyl-B(OH)$_2$ or aryl-B(OH)$_2$), boric acid (i.e., H$_3$BO$_3$), tetraboric acid (i.e., H$_2$B$_4$O$_7$), metaboric acid (i.e., HBO$_2$), boron anhydrides, boron amides and various esters of such boron acids. The use of complexes of boron trihalide with ethers, organic acids, inorganic acids, or hydrocarbons is a convenient means of introducing the boron reactant into the reaction mixture. Such complexes are known and are exemplified by boron-trifluoride-triethyl ester, boron trifluoride-phosphoric acid, boron trichloride-chloroacetic acid, boron tribromide-dioxane, and boron trifluoride-methyl ethyl ether.

Specific examples of boronic acids include methyl boronic acid, phenyl-boronic acid, cyclohexyl boronic acid, p-heptylphenyl boronic acid and dodecyl boronic acid.

The boron acid esters include especially mono-, di-, and tri-organic esters of boric acid with alcohols or phenols such as, e.g., methanol, ethanol, isopropanol, cyclohexanol, cyclopentanol, 1-octanol, 2-octanol, dodecanol, behenyl alcohol, oleyl alcohol, stearyl alcohol, benzyl alcohol, 2-butyl cyclohexanol, ethylene glycol, propylene glycol, trimethylene glycol, 1,3-butanediol, 2,4-hexanediol, 1,2-cyclohexanediol, 1,3-octanediol, glycerol, pentaerythritol, diethylene glycol, carbitol, Cellosolve, triethylene glycol, tripropylene glycol, phenol, naphthol, p-butylphenol, o,p-diheptylphenol, n-cyclohexylphenol, 2,2-bis-(p-hydroxyphenyl)propane, polyisobutene (molecular weight of 1500)-substituted phenol, ethylene chlorohydrin, o-chlorophenol, m-nitrophenol, 6-bromo-octanol, and 7-keto-decanol. Lower alcohols, 1,2-glycols, and 1-3-glycols, i.e., those having less than about 8 carbon atoms are especially useful for preparing the boric acid esters for the purpose of this invention.

Methods for preparing the esters of boron acid are known and disclosed in the art (such as "Chemical Reviews," pp. 959–1064, Vol. 56). Thus, one method involves the reaction of boron trichloride with 3 moles of an alcohol or a phenol to result in a tri-organic borate. Another method involves the reaction of boric oxide with an alcohol or a phenol. Another method involves the direct esterification of tetra boric acid with 3 moles of an alcohol or a phenol. Still another method involves the direct esterification of boric acid with a glycol to form, e.g., a cyclic alkylene borate.

The reaction of the acylated nitrogen intermediate with the boron compounds can be effected simply by mixing the reactants at the desired temperature. The use of an inert solvent is optional although it is often desirable, especially when a highly viscous or solid reactant is present in the reaction mixture. The inert solvent may be a hydrocarbon such as benzene, toluene, naphtha, cyclohexane, n-hexane, or mineral oil. The temperature of the reaction may be varied within wide ranges. Ordinarily it is preferably between about 50° C. and about 250° C. In some instances it may be 25° C. or ever lower. The upper limit of the temperature is the decomposition point of the particular reaction mixture and/or product.

The reaction is usually complete within a short period such as 0.5 to 6 hours. After the reaction is complete, the product may be dissolved in the solvent and the resulting solution purified by centrifugation or filtration if it appears to be hazy or contain insoluble substances. Ordinarily the product is sufficiently pure so that further purification is unnecessary or optional.

The reaction of the acylated nitrogen compositions with the boron compounds results in a product containing boron and substantially all of the nitrogen originally present in the nitrogen reactant. It is believed that the reaction results in the formation of a complex between boron and nitrogen. Such complex may involve in some instances more than one atomic proportion of boron with one atomic proportion of nitrogen and in other instances more than one atomic proportion of nitrogen with one atomic proportion of boron. The nature of the complex is not clearly understood.

Inasmuch as the precise stoichiometry of the complex formation is not known, the relative proportions of the reactants to be used in the process are based primarily upon the consideration of utility of the products for the purposes of this invention. In this regard, useful products are obtained from reaction mixtures in which the reactants are present in relative proportions as to provide from about 0.1 atomic proportions of boron for each mole of the acylated nitrogen composition used to about 10 atomic proportions of boron for each atomic proportion of nitrogen of said acylated nitrogen composition used. The preferred amounts of reactants are such as to provide from about 0.5 atomic proportion of boron for each mole of the acylated nitrogen composition to about 2 atomic proportions of boron for each atomic proportion of nitrogen used. To illustrate, the amount of a boron compound having one boron atom per molecule to be used with one mole of an acylated nitrogen composition having five nitrogen atoms per molecule is within the range from about 0.1 mole to about 50 moles, preferably from about 0.5 mole to about 10 moles.

The following examples are illustrative of the process for preparing the nitrogen-containing and the nitrogen- and boron-containing compositions useful in this invention:

EXAMPLE B-1

A polyisobutenyl succinic anhydride is prepared by the reaction of a chlorinated polyisobutylene with maleic anhydride at 200° C. The polyisobutenyl group has an average molecular weight of 850 and the resulting alkenyl succinic anhydride is found to have an acid number of 113 (corresponding to an equivalent weight of 500). To a mixture of 500 grams (1 equivalent) of this polyisobutenyl succinic anhydride and 160 grams of toluene there is added at room temperature 35 grams (1 equivalent) of diethylene triamine. The addition is made portionwise throughout a period of 15 minutes, and an initial exothermic reaction caused the temperature to rise to 50° C. The mixture then is heated and a water-toluene azeotrope distilled from the mixture. When no more water distills, the mixture is heated to 150° C. at reduced pressure to remove the toluene. The residue is diluted with 350 grams of mineral oil and this solution is found to have a nitrogen content of 1.6%.

EXAMPLE B-2

The procedure of Example B-1 is repeated using 31 grams (1 equivalent) of ethylene diamine as the amine reactant. The nitrogen content of the resulting product is 1.4%.

EXAMPLE B-3

The procedure of Example B-1 is repeated using 55.5 grams (1.5 equivalents) of an ethylene amine mixture having a composition corresponding to that of triethylene tetramine. The resulting product has a nitrogen content of 1.9%.

EXAMPLE B-4

The procedure of Example B-1 is repeated using 55.0 grams (1.5 equivalents) of triethylene tetramine as the amine reactant. The resulting product has a nitrogen content of 2.9%.

EXAMPLE B-5

To a mixture of 140 grams of toluene and 400 grams (0.78 equivalent) of a polyisobutenyl succinic anhydride (having an acid number of 109 and prepared from maleic anhydride and the chlorinated polyisobutylene of Example B-1) there is added at room temperature 63.6 grams (1.55 equivalents) of a commercial ethylene amine mixture having an average composition corresponding to that of tetraethylene pentamine. The mixure is heated to distill the water-toluene azeotrope and then to 150° C. at reduced pressure to remove the remaining toluene. The residual polyamide has a nitrogen content of 4.7%.

EXAMPLE B-6

A polyisobutenyl succinic anhydride having an acid number of 105 and an equivalent weight of 540 is prepared by the reaction of a chlorinated polyisobutylene (having an average molecular weight of 1050 and a chlorine content of 4.3%) and maleic anhydride. To a mixture of 300 parts by weight of the polyisobutenyl succinic anhydride and 160 parts by weight of mineral oil there is added at 65°–95° C. an equivalent amount (25 parts by weight) of the commercial ethylene amine mixture of Example B-5. This mixture then is heated to 150° C. to distill all of the water formed in the reaction. Nitrogen is bubbled through the mixture at this temperature to insure removal of the last traces of water. The residue is diluted by 79 parts by weight of mineral oil and this oil solution found to ahve a nitrogen content of 1.6%.

EXAMPLE B-7

A polypropylene-substituted succinic anhydride having an acid number of 84 is prepared by the reaction of a chlorinated polypropylene having a chlorine content of 3% and molecular weight of 1200 with maleic anhydride. A mixture of 813 grams of the polypropylene-substituted succinic anhydride, 50 grams of a commercial ethylene amine mixture having an average composition corresponding to that of tetraethylene pentamine and 566 grams of mineral oil is heated at 150° C. for 5 hours. The residue is found to have a nitrogen content of 1.18%.

EXAMPLE B-8

An acylated nitrogen composition is prepared according to the procedure of Example B-1 except that the reaction mixture consists of 3880 grams of the polyisobutenyl succinic anhydride, 376 grams of a mixture of triethylene tetramine and diethylene triamine (75:25 weight ratio), and 2785 grams of mineral oil. The product is found to have a nitrogen content of 2%.

EXAMPLE B-9

An acylated nitrogen composition is prepared according to the procedure of Example B-1 except that the reaction mixture consists of 1385 grams of the polyisobutenyl succinic anhydride, 179 grams of a mixture of triethylene tetramine and diethylene triamine (75:25 weight ratio), and 1041 grams of mineral oil. The product is found to have a nitrogen content of 2.55%.

EXAMPLE B-10

An acylated nitrogen composition is prepared according to the procedure of Example B-7 except that the polyisobutene-substituted succinic anhydride of Example B-1 (1 equivalent for 1.5 equivalents of the amine reactant) is substituted for the polypropylene-substituted succinic anhydride used.

EXAMPLE B-11

An acylated nitrogen composition is prepared according to the procedure of Example B-7 except that the polyisobutene-substituted succinic anhydride of Example B-1 (1 equivalent for 2 equivalents of the amine reactant) is substituted for the polypropylene-substituted succinic anhydride used.

EXAMPLE B-12

An acylated nitrogen composition is prepared according to the procedure of Example B-4 except that the commercial ethylene amine mixture (1.5 equivalent per equivalent of the anhydride) of Example B-6 is substituted for the triethylene tetramine used.

EXAMPLE B-13

An acylated nitrogen composition is prepared according to the procedure of Example B-7 except that the polyisobutene-substituted succinic anhydride of Example B-1 (1 equivalent for 1 equivalent of the amine reactant) is substituted for the polypropylene-substituted succinic anhydride. The composition is found to have a nitrogen content of 1.5%.

EXAMPLE B-14

A mixture of 510 parts (0.28 mole) of polyisobutene (Mn=1854; Mw=5325) and 59 parts (0.59 mole) of maleic anhydride is heated to 110° C. This mixture is heated to 190° C. in 7 hours during which 43 parts (0.6 mole) of gaseous chlorine is added beneath the surface. At 190°–192° C. an additional 11 parts (0.16 mole) of chlorine is added over 3.5 hours. The reaction mixture is stripped by heating at 190°–193° C. with nitrogen blowing for 10 hours. The residue is the desired polyisobutene-substituted succinic acylating agent having a saponification equivalent number of 87 as determined by ASTM procedure D-94.

A mixture is prepared by the addition of 10.2 parts (0.25 equivalent) of a commercial mixture of ethylene polyamines having from about 3 to about 10 nitrogen atoms per molecule to 113 parts of mineral oil and 161 parts (0.25 equivalent) of the substituted succinic acylating agent at 130° C. The reaction mixture is heated to 150° C. in 2 hours and stripped by blowing with nitrogen. The reaction mixture is filtered to yield the filtrate as an oil solution of the desired product.

EXAMPLE B-15

A mixture of 1000 parts (0.495 mole) of polyisobutene (Mn=2020; Mw=6049) and 115 parts (1.17 moles) of maleic anhydride is heated to 110° C. This mixture is heated to 184° in 6 hours during which 85 parts (1.2 moles) of gaseous chlorine is added beneath the surface. At 184°–189° C., an additional 59 parts (0.83 mole) of chlorine is added over 4 hours. The reaction mixture is stripped by heating at 186°–190° C. with nitrogen blowing for 26 hours. The residue is the desired polyisobutene-substituted succinic acylating agent having a saponification equivalent number of 87 as determined by ASTM procedure D-94.

A mixture is prepared by the addition of 57 parts (1.38 equivalents) of a commercial mixture of ethylene polyamines having from about 3 to 10 nitrogen atoms per molecule to 1067 parts of mineral oil and 893 parts (1.38 equivalents) of the substituted succinic acylating agent at 140°–145° C. The reaction mixture is heated to 155° C. in 3 hours and stripped by blowing with nitrogen. The reaction mixture is filtered to yield the filtrate as an oil solution of the desired product.

EXAMPLE B-16

A mixture is prepared by the addition of 18.2 parts (0.433 equivalent) of a commercial mixture of ethylene polyamines having from about 3 to 10 nitrogen atoms per molecule to 392 parts of mineral oil and 348 parts (0.52 equivalent) of the substituted succinic acylating agent prepared in Example B-15 at 140° C. The reaction mixture is heated to 150° C. in 1.8 hours and stripped by blowing with nitrogen. The reaction mixture is filtered to yield the filtrate as an oil solution of the desired product.

EXAMPLE B-17

To 600 grams (1 atomic proportion of nitrogen) of the acylated nitrogen composition prepared according to the process of Example B-13 there is added 45.5 grams (0.5 atomic proportion of boron) of boron trifluoridediethyl ether complex (1:1 molar ratio) at 60°–75° C. The resulting mixture is heated to 103° C. and then at 110° C./30 mm. to distill off all volatile components. The residue is found to have a nitrogen content of 1.44% and a boron content of 0.49%.

EXAMPLE B-18

A mixture of 62 grams (1 atomic proportion of boron) of boric acid and 1645 grams (2.35 atomic proportions of nitrogen) of the acylated nitrogen composition obtained by the process of Example B-8 is heated at 150° C. in nitrogen atmosphere for 6 hours. The mixture is then filtered and the filtrate is found to have a nitrogen content of 1.94% and a boron content of 0.33%.

EXAMPLE B-19

An oleyl ester of boric acid is prepared by heating an equi-molar mixture of oleyl alcohol and boric acid in toluene at the reflux temperature while water is removed azeotropically. The reaction mixture is then heated to 150° C./20 mm. and the residue is the ester having a boron content of 3.2% and a saponification number of 62. A mixture of 344 grams (1 atomic proportion of boron) of the ester and 1645 grams (2.35 atomic proportions of nitrogen) of the acylated nitrogen composition obtained by the process of Example B-8 is heated at 150° C. for 6 hours and then filtered. The filtrate is found to have a boron content of 0.6% and a nitrogen content of 1.74%.

EXAMPLE B-20

A mixture of 372 (6 atomic proportions of boron) of boric acid and 3111 grams (6 atomic proportions of nitrogen) of the acylated nitrogen composition obtained by the process of Example B-11 is heated at 150° C. for 3 hours and then filtered. The filtrate is found to have a boron content of 1.64% and a nitrogen content of 2.56%.

EXAMPLE B-21

Boric acid (124 grams, 2 atomic proportions of boron) is added to the acylated nitrogen composition (556 grams, 1 atomic proportion of nitrogen) obtained according to the procedure of Example B-11. The resulting mixture is heated at 150° C. for 3.5 hours and filtered at that temperature. The filtrate is found to have a boron compound of 3.23% and a nitrogen content of 2.3%.

EXAMPLE B-22

A mixture of 62 parts of boric acid and 2720 parts of the oil solution of the product prepared in Example B-15 is heated at 150° C. under nitrogen for 6 hours. The reaction mixture is filtered to yield the filtrate as an oil solution of the desired boron-containing product.

EXAMPLE B-23

An oleyl ester of boric acid is prepared by heating an equimolar mixture of oleyl alcohol and boric acid in toluene at the reflux temperature while water is removed azeotropically. The reaction mixture is then heated to 150° C. under vacuum and the residue is the ester having a boron content of 3.2% and a saponification number of 62. A mixture of 344 parts of the heater and 2720 parts of the oil solution of the product prepared in Example B-15 is heated at 150° C. for 6 hours and then filtered. The filtrate is an oil solution of the desired boron-containing product.

EXAMPLE B-24

Boron trifluoride (34 parts) is bubbled into 2190 parts of the oil solution of the product prepared in Example B-16 at 80° C. within a period of 3 hours. The resulting mixture is blown with nitrogen at 70°–80° C. for 2 hours to yield the residue as an oil solution of the desired product.

Generally, the lubricants and functional fluids of the present invention contain an amount of the borated amine salt (A) and optionally, the nitrogen-containing composition (B) to provide the lubricants and functional fluids with the desired properties such as improved extreme pressure properties and high temperature stability. Normally, this amount will be from about 0.1 to about 10% by weight of the combination of (A) and (B) and preferably from about 0.5 to about 7.5% of the total weight of the fluid. The relative amounts of borated amine salt (A) and nitrogen-containing composition (B) contained in the lubricant may vary over a wide range although the weight ratio of (A):(B) generally is from about 0.1:1 to about 10:1. In a more preferred embodiment, the weight ratio (A):(B) is from about 1:1 to about 4:1.

The invention also contemplates the use of other additives in the lubricating and functional fluid compositions of this invention. Such additives include, for example, detergents and dispersants of the ash-producing or ashless type, corrosion- and oxidation-inhibiting agents, pour point depressing agents, extreme pressure agents, antiwear agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature of about 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-betanaphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a nonvolatile material such as boric oxide or phosphorus pentoxide; however, it does not ordinarily contain metal and therefore does not yield a metal-containing ash on combustion. Many types are known in the art, and any of them are suitable for use in the lubricant compositions of this invention. The following are illustrative:

(1) Reaction products of relatively high molecular weight aliphatic or alicyclic halides with amines, preferably oxyalkylene polyamines. These may be characterized as "amine dispersants" and examples thereof are described for example, in the following U.S. Pat. Nos. 3,275,554, 3,438,757, 3,454,555, 3,565,804.

(2) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Patents are illustrative: U.S. Pat. Nos. 2,459,112, 2,962,442, 2,984,550, 3,036,003, 3,166,516, 3,236,770, 3,355,270, 3,368,972, 3,413,347, 3,442,808, 3,448,047, 3,454,497, 3,459,661, 3,461,172, 3,493,520, 3,539,633, 3,558,743, 3,586,629, 3,591,598, 3,600,372, 3,634,515, 3,649,229, 3,697,574, 3,725,277, 3,725,480, 3,726,882, 3,980,569.

(3) Products obtained by post-treating the amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.: 3,036,003, 3,087,936, 3,200,107, 3,216,936, 3,254,025, 3,256,185, 3,278,550, 3,280,234, 3,281,428, 3,282,955, 3,312,619, 3,366,569, 3,367,943, 3,373,111, 3,403,102, 3,442,808, 3,455,831, 3,455,832, 3,493,520, 3,502,677, 3,513,093, 3,533,945, 3,539,633, 3,573,010, 3,579,450, 3,591,598, 3,600,372, 3,639,242, 3,649,229, 3,649,659, 3,658,836, 3,697,574, 3,702,757, 3,703,536, 3,704,308, 3,708,422.

(4) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.: 3,329,658, 3,449,250, 3,519,565, 3,666,730, 3,687,849, 3,702,300.

The above-noted patents are incorporated by reference herein for their disclosures of ashless dispersants.

Auxiliary extreme pressure agents and corrosion- and oxidation-inhibiting agents which may be included in the lubricants and functional fluids of the invention are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Many of the above-mentioned auxiliary extreme pressure agents and corrosion-oxidation inhibitors also serve as antiwear agents. Zinc dialkylphosphorodithioates are a well known example.

Pour point depressants are a particularly useful type of additive often included in the lubricating oils described herein. The use of such pour point depressants in oil-based compositions to improve low temperature properties of oil-based compositions is well known in the art. See, for example, page 8 of "Lubricant Additives" by C. V. Smalheer and R. Kennedy Smith (Leizus-Hiles Co. publishers, Cleveland, Ohio, 1967).

Examples of useful pour point depressants are polymethacrylates; polyacrylates; polyacrylamides; condensation products of haloparaffin waxes and aromatic compounds; vinyl carboxylate polymers; and terpolymers of dialkylfumarates, vinyl esters of fatty acids and alkyl vinyl ethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are herein incorporated by reference for their relevant disclosures.

Anti-foam agents are used to reduce or prevent the formation of stable foam. Typical anti-foam agents include silicones or organic polymers. Additional anti-foam compositions are described in "Foam Control Agents", by Henry T. Kerner (Noyes Data Corporation, 1976), pages 125-162.

The following examples illustrate the lubricant compositions of the invention.

|  | Parts by Wt. |
|---|---|
| Lubricant A | |
| Base oil | 98 |
| Product of Example A-3 | 2.00 |
| Lubricant B | |
| Base oil | 98 |
| Product of Example A-1 | 1.00 |
| Product of Example B-1 | 1.00 |
| Lubricant C | |
| Base Oil | 96.75 |
| Product of Example A-14 | 1.25 |
| Product of Example B-17 | 2.00 |
| Lubricant D | |
| Base Oil | 97.50 |
| Product of Example A-4 | 1.00 |
| Product of Example B-14 | 1.50 |
| Lubricant E (ATF) | |
| Polyisobutylene (Mn 900) | 35 |
| Product of Example A-8 | 3.5 |
| Product of Example B-19 | 1.5 |
| Commercially available naphthenic oil having a viscosity at 40° C. of about 3.5 CKS | 29 |
| Reaction product of polyisobutenyl succinic anhydride with ethylene polyamine and carbon disulfide | 9.52 |
| Seal sweller prepared as in U.S. Pat. No. 4,029,587 | 1.67 |
| Silicone antifoam agent | 1.33 |

| Lubricants F, G and H (Hydraulic Fluids) | | | |
|---|---|---|---|
|  | F | G | H |
| 100 Neutral Mineral Oil | 92.2 | 88.17 | 91.11 |
| Product of Example A-2 | 0.67 | 1.10 | 0.85 |
| Product of Example B-20 | 0.50 | 0.70 | 0.50 |
| Polyisobutylene (Mn = 1400) | 4.24 | 6.52 | 4.89 |
| Alkylate 230 (a product of Monsanto identified as an alkylated benzene having a molecular weight of about 260) | 1.05 | 1.61 | 1.21 |
| Acryloid 150 (a product of Rohm & Haas identified as a methacrylate copolymer) | 0.052 | 0.081 | 0.060 |
| Acryloid 156 (a product of Rohm & Haas identified as a methacrylate copolymer) | 0.155 | 0.238 | 0.179 |
| Zinc di(2-ethylhexyl) dithiophosphate | 0.371 | 0.53 | 0.371 |
| Sodium petroleum sulfonate | 0.0506 | 0.03 | 0.0506 |
| Antioxidant 732 (product of Ethyl identified as alkylated phenol) | 0.151 | 0.18 | 0.151 |
| Tolad 370 (product of Petrolite identified as a solution of a polyglycol in aromatic hydrocarbons) | 0.01 | 0.008 | 0.01 |
| Sulfurized calcium salt of dodecyl phenol | 0.05 | 0.07 | 0.05 |
| Tolyltriazole | 0.00165 | 0.001 | 0.00165 |
| Acrylate terpolymer derived from 2-ethylhexyl acrylate, ethyl acrylate and vinyl acetate | 0.015 | — | 0.015 |
| Diluent oil | 0.48 | 0.76 | 0.569 |

The lubricant compositions of the present invention may be in the form of lubricating oils and greases in which any of the above-described oils of lubricating viscosity can be employed as a vehicle. Where the lubricant is to be used in the form of a grease, the lubricating oil generally is employed in an amount sufficient to balance the total grease composition and generally, the grease compositions will contain various quantities of thickening agents and other additive components to provide desirable properties.

A wide variety of thickening agents can be used in the preparation of the greases of this invention. Included among the thickening agents are alkali and alkaline earth metal soaps of fatty acids and fatty materials having from about 12 to about 30 carbon atoms. The metals are typified by sodium, lithium, calcium and barium. Examples of fatty materials include stearic acid, hydroxy stearic acid, stearin, oleic acid, palmetic acid, myristic acid, cottonseed oil acids, and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Particularly useful thickening agents employed in the grease compositions are essentially hydrophilic in character, but which have been converted into a hydrophobic condition by the introduction of long chain hydrocarbon radicals onto the surface of the clay particles prior to their use as a component of a grease composition, as, for example, by being subjected to a preliminary treatment with an organic cationic surface-active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, and is believed to require no further discussion. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3% to 15% by weight of the total grease composition.

The invention also includes aqueous compositions characterized by an aqueous phase with at least one borated amine salt (A) dispersed or dissolved in said aqueous phase. The aqueous system may also contain component (B). Preferably, this aqueous phase is a continuous aqueous phase, although in some embodiments the aqueous phase can be a discontinuous phase. These aqueous compositions usually contain at least about 25% by weight water. Such aqueous compositions encompass both concentrates containing about 25% to about 80% by weight, preferably from about 40% to about 65% water; and water-based functional fluids containing generally over about 80% by weight of water. The concentrates generally contain from about 10% to about 90% by weight of component (A) or the mixture of components (A) and (B). The water-based functional fluids generally contain from about 0.05% to about 15% by weight of (A) or the mixture of (A) and (B). The concentrates generally contain less than about 50%, preferably less than about 25%, more preferably less than about 15%, and still more preferably less than about 6% hydrocarbon oil. The water-based functional fluids generally contain less than about 15%, preferably less than about 5%, and more preferably less than about 2% hydrocarbon oil.

These concentrates and water-based functional fluids can optionally include other conventional additives commonly employed in water-based functional fluids. These other additives include surfactants; thickeners; oil-soluble, water-insoluble functional additives such as anti-wear agents, extreme pressure agents, dispersants, etc.; and supplemental additives such as corrosion-inhibitors, shear stabilizing agents, bactericides, dyes, water-softeners, odor masking agents, anti-foam agents and the like.

The concentrates are analogous to the water-based functional fluids except that they contain less water and proportionately more of the other ingredients. The concentrates can be converted to water-based functional fluids by dilution with water. This dilution is usually done by standard mixing techniques. This is often a convenient procedure since the concentrate can be shipped to the point of use before additional water is added. Thus, the cost of shipping a substantial amount of the water in the final water-based functional fluid is saved. Only the water necessary to formulate the concentrate (which is determined primarily by ease of handling and convenience factors), need be shipped.

Generally these water-based functional fluids are made by diluting the concentrates with water, wherein the ratio of water to concentrate is usually in the range of about 80:20 to about 99:1 by weight. As can be seen when dilution is carried out within these ranges, the final water-based functional fluid contains, at most, an insignificant amount of hydrocarbon oil.

In various preferred embodiments of the invention, the water-based functional fluids are in the form of solutions while in other embodiments they are in the form of micelle dispersions or microemulsions which appear to be true solutions. Whether a solution, micelle dispersion or a microemulsion is formed is dependent, inter alia, on the particular components employed.

Also included within this invention are methods for preparing aqueous compositions, including both concentrates and water-based functional fluids, containing other conventional additives commonly employed in water-based functional fluids. These methods comprise the steps of:

(1) mixing component (A) or a mixture of components (A) and (B) of the invention with such other conventional additives either simultaneously or sequentially to form a dispersion or solution; optionally (2) combining said dispersion or solution with water to form said aqueous concentrate; and/or (3) diluting said dispersion or solution, or concentrate with water wherein the total amount of water used is in the amount required to provide the desired concentration of the components of the invention and other functional additives in said concentrates or said water-based functional fluids.

These mixing steps are preferably carried out using conventional equipment and generally at room or slightly elevated temperatures, usually below 100° C. and often below 50° C. As noted above, the concentrate can be formed and then shipped to the point of use where it is diluted with water to form the desired water-based functional fluid. In other instances the finished water-based functional fluid can be formed directly in the same equipment used to form the concentrate or the dispersion or solution.

The surfactants that are useful in the aqueous compositions of the invention can be of the cationic, anionic, nonionic or amphoteric type. Many such surfactants of each type are known to the art. See, for example, McCutcheon's "Emulsifiers & Detergents", 1981, North American Edition, published by McCutcheon Division, MC Publishing Co., Glen Rock, N.J., U.S.A., which is hereby incorporated by reference for its disclosures in this regard.

Among the nonionic surfactant types are the alkylene oxide-treated products, such as ethylene oxide-treated phenols, alcohols, esters, amines and amides. Ethylene oxide/propylene oxide block copolymers are also useful nonionic surfactants. Glycerol esters and sugar esters are also known to be nonionic surfactants. A typical nonionic surfactant class useful with the present invention are the alkylene oxide-treated alkyl phenols such as the ethylene oxide alkyl phenol condensates sold by the Rohm & Haas Company. A specific example of these is Triton X-100 which contains an average of 9-10 ethylene oxide units per molecule, has an HLB value of about 13.5 and a molecular weight of about 628. Many other suitable nonionic surfactants are known; see, for example, the aforementioned McCutcheon's as well as the treatise "Non-Ionic Surfactants" edited by Martin J. Schick, M. Dekker Co., New York, 1967, which is herein incorporated by reference for its disclosures in this regard.

As noted above, cationic, anionic and amphoteric surfactants can also be used. Generally, these are all hydrophilic surfactants. Anionic surfactants contain negatively charged polar groups while cationic surfactants contain positively charged polar groups. Amphoteric dispersants contain both types of polar groups in the same molecule. A general survey of useful surfactants is found in Kirk-Othmer Encyclopedia of Chemical Technology, Second Edition, Volume 19, page 507 et seq. (1969, John Wiley and Son, New York) and the aforementioned compilation published under the name of McCutcheon's. These references are both hereby incorporated by reference for their disclosures relating to cationic, amphoteric and anionic surfactants.

Among the useful anionic surfactant types are the widely known carboxylate soaps, organo sulfates, sulfonates, sulfocarboxylic acids and their salts, and phosphates. Useful cationic surfactants include nitrogen compounds such as amine oxides and the well-known quaternary ammonium salts. Amphoteric surfactants include amino acid-type materials and similar types. Various cationic, anionic and amphoteric dispersants are available from the industry, particularly from such companies as Rohm & Haas and Union Carbide Corporation, both of America. Further information about anionic and cationic surfactants also can be found in the texts "Anionic Surfactants", Parts II and III, edited by W. M. Linfield, published by Marcel Dekker, Inc. New York, 1976 and "Cationic Surfactants", edited by E. Jungermann, Marcel Dekker, Inc., New York, 1976. Both of these references are incorporated by reference for their disclosures in this regard.

These surfactants, when used, are generally employed in effective amounts to aid in the dispersal of the various additives, particularly the functional additives discussed below, in the concentrates and water-based functional fluids of the invention. Preferably, the concentrates can contain up to about 75% by weight, more preferably from about 10% to about 75% by weight of one or more of these surfactants. The water-based functional fluids can contain up to about 15% by weight, more preferably from about 0.05% to about 15% by weight of one or more of these surfactants.

Often the aqueous compositions of this invention contain at least one thickener for thickening said compositions. Generally, these thickeners can be polysaccharides, synthetic thickening polymers, or mixtures of two or more of these. Among the polysaccharides that are useful are natural gums such as those disclosed in "Industrial Gums" by Whistler and B. Miller, published by Academic Press, 1959. Disclosures in this book relating to water-insoluble thickening natural gums is hereby incorporated by reference. Specific examples of such gums are gum agar, guar gum, gum arabic, algin, dextrans, xanthan gum and the like. Also among the polysaccharides that are useful as thickeners for the aqueous compositions of this invention are cellulose ethers and esters, including hydroxy hydrocarbyl cellulose and hydrocarbylhydroxy cellulose and its salts. Specific examples of such thickeners are hydroxyethyl cellulose and the sodium salt of carboxymethyl cellulose. Mixtures of two or more of any such thickeners are also useful.

It is a general requirement that the thickener used in the aqueous compositions of the present invention be soluble in both cold (10° C.) and hot (about 90° C.) water. This excludes such materials as methyl cellulose which is soluble in cold water but not in hot water. Such hot-water-insoluble materials, however, can be used to perform other functions such as providing lubricity to the aqueous compositions of this invention.

These thickeners can also be synthetic thickening polymers. Many such polymers are known to those of skill in the art. Representative of them are polyacrylates, polyacrylamides, hydrolyxed vinyl esters, water-soluble homo- and interpolymers of acrylamidoalkane sulfonates containing 50 mole percent at least of acryloamido alkane sulfonate and other comonomers such as acrylonitrile, styrene and the like. Poly-n-vinyl pyrrolidones, homo- and copolymers as well as water-soluble salts of styrene, maleic anhydride and isobutylene maleic anhydride copolymers can also be used as thickening agents.

Other useful thickeners are known to those of skill in the art and many can be found in the list in the aforementioned MuCutcheon Publication: "Functional Materials," 1976, pp. 135-147, inclusive. The disclosures therein, relative to water-soluble polymeric thickening agents meeting the general requirements set forth above are hereby incorporated by reference.

Preferred thickeners, particularly when the compositions of the invention are required to be stable under high shear applications, are the water-dispersible reaction products formed by reacting at least one hydrocarbyl-substituted succinic acid and/or anhydride represented by the formula

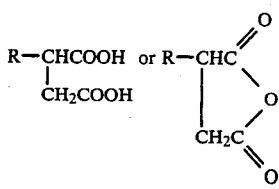

wherein R is a hydrocarbyl group of from about 8 to about 40 carbon atoms, with at least one water-dispersible amine terminated poly(oxyalkylene) or at least one water-dispersible hydroxy-terminated polyoxyalkylene. R preferably has from about 8 to about 30 carbon atoms, more preferably from about 12 to about 24 carbon atoms, still more preferably from about 16 to about 18 carbon atoms. In a preferred embodiment, R is represented by the formula

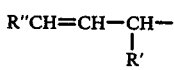

wherein R' and R" are independently hydrogen or straight chain or substantially straight chain hydrocarbyl groups, with the proviso that the total number of carbon atoms in R is within the above-indicated ranges. Preferably R' and R" are alkyl or alkenyl groups. In a particularly advantageous embodiment, R has from about 16 to about 18 carbon atoms, R' is hydrogen or an alkyl group of from 1 to about 7 carbon atoms or an alkenyl group of from 2 to about 7 carbon atoms, and R" is an alkyl or alkenyl group of from about 5 to about 15 carbon atoms.

The water-dispersible amine terminated poly(oxyalkylene)s are preferably alpha omega diamino poly(oxyethylene)s, alpha omega diamino poly(oxypropylene) poly(oxyethylene) poly(oxypropylene)s or alpha omega diamino propylene oxide capped poly(oxyethylene)s. The amine-terminated poly(oxyalkylene) can also be a urea condensate of such alpha omega diamino poly(oxyethylene)s, alpha omega diamino poly(oxypropylene) poly(oxyethylene) poly-(oxypropylene)s or alpha omega diamino propylene oxide capped poly(oxyethylene)s. The amine-terminated poly(oxyalkylene) can also be a polyamino (e.g., triamino, tetramino, etc.) polyoxyalkylene provided it is amine-terminated and it is water-dispersible.

Examples of water-dispersible amine-terminated poly(oxyalkylene)s that are useful in accordance with the present invention are disclosed in U.S. Pat. Nos. 3,021,232; 3,108,011; 4,444,566; and U.S. Pat. No. Re. 31,522. The disclosures of these patents are incorporated herein by reference. Water-dispersible amine terminated poly(oxyalkylene)s that are useful are commercially available from the Texaco Chemical Company under the trade name Jeffamine.

The water-dispersible hydroxy-terminated polyoxyalkylenes are constituted of block polymers of propylene oxide and ethylene oxide, and a nucleus which is derived from organic compounds containing a plurality of reactive hydrogen atoms. The block polymers are attached to the nucleus at the sites of the reactive hydrogen atoms. Examples of these compounds include the hydroxy-terminated polyoxyalkylenes which are represented by the formula

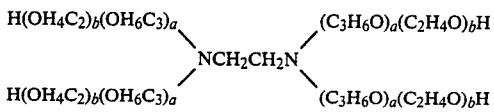

wherein a and b are integers such that the collective molecular weight of the oxypropylene chains range from about 900 to about 25,000, and the collective weight of the oxyethylene chains constitute from about 20% to about 90%, preferably from about 25% to about 55% by weight of the compound. These compounds are commercially available from BASF Wyandotte Corporation under the tradename "Tetronic". Additional examples include the hydroxy-terminated polyoxyalkylenes represented by the formula

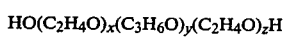

wherein y is an integer such that the molecular weight of the oxypropylene chain is at least about 900, and x and z are integers such that the collective weight of the oxyethylene chains constitute from about 20% to about 90% by weight of the compound. These compounds preferably have a molecular weight in the range of about 1100 to about 14,000. These compounds are commercially available from BASF Wyandotte Corporation under the tradename "Pluronic". Useful hydroxy-terminated polyoxyalkylenes are disclosed in U.S. Pat. Nos. 2,674,619 and 2,979,528, which are incorporated herein by reference.

The reaction between the carboxylic agent and the amine- or hydroxy-terminated polyoxyalkylene can be carried out at a temperature ranging from the highest of the melt temperatures of the reaction components up to the lowest of the decomposition temperatures of the reaction components or products. Generally, the reaction is carried out at a temperature in the range of about 60° C. to about 160° C., preferably about 120° C. to about 160° C. The ratio of equivalents of carboxylic agent to polyoxyalkylene preferably ranges from about 0.1:1 to about 8:1, preferably about 1:1 to about 4:1, and advantageously about 2:1. The weight of an equivalent of the carboxylic agent can be determined by dividing its molecular weight by the number of carboxylic functions present. The weight of an equivalent of the amine-terminated polyoxyalkylene can be determined by dividing its molecular weight by the number of terminal amine groups present. The weight of an equivalent of the hydroxy-terminated polyoxyalkylene can be determined by dividing its molecular weight by the number of terminal terminal hydroxyl groups present. The number of terminal amine and hydroxyl groups can usually be determined from the structural formula of the polyoxyalkylene or empirically through well known procedures. The amide/acids and ester/acids formed by the reaction of the carboxylic agent and amine-terminated or hydroxy-terminated polyoxyalkylene can be neutralized with, for example, one or more alkali metals, one or more amines, or a mixture thereof, and thus converted to amide/salts or ester/salts, respectively. Additionally, if these amide/acids or ester/acids are added to concentrates or functional fluids containing alkali metals or amines, amide/salts or ester/salts usually form, in situ.

South African Pat. No. 85/0978 is incorporated herein by reference for its teachings with respect to the use of hydrocarbyl-substituted succinic acid or anhydride/hydroxy-terminated poly(oxyalkylene) reaction products as thickeners for aqueous compositions.

When the thickener is formed using an amine-terminated poly(oxyalkylene), the thickening characteristics of said thickener can be enhanced by combining it with at least one surfactant. Any of the surfactants identified above under the subtitle "Surfactants" can be used in this regard. When such surfactants are used, the weight ratio of thickener to surfactant is generally in the range of from about 1:5 to about 5:1, preferably from about 1:1 to about 3:1.

Typically, the thickener is present in a thickening amount in the aqueous compositions of this invention. When used, the thickener is preferably present at a level of up to about 70% by weight, preferably from about 20% to about 50% by weight of the concentrates of the invention. The thickener is preferably present at a level in the range of from about 1.5% to about 10% by weight, preferably from about 3% to about 6% by weight of the functional fluids of the invention.

The functional additives that can be used in the aqueous systems are typically oil-soluble, water-insoluble additives which function in conventional oil-based systems as extreme pressure agents, anti-wear agents, load-carrying agents, dispersants, friction modifiers, lubricity agents, etc. They can also function as anti-slip agents, film formers and friction modifiers. As is well known, such additives can function in two or more of the above-mentioned ways; for example, extreme pressure agents often function as load-carrying agents.

The term "oil-soluble, water-insoluble functional additive" refers to a functional additive which is not soluble in water above a level of about 1 gram per 100 milliliters of water at 25° C., but is soluble in mineral oil to the extent of at least 1 gram per liter at 25° C.

These functional additives can also include certain solid lubricants such as graphite, molybdenum disulfide and polytetrafluoroethylene and related solid polymers.

These functional additives can also include frictional polymer formers. Briefly, these are potential polymer forming materials which are dispersed in a liquid carrier at low concentration and which polymerize at rubbing or contacting surfaces to form protective polymeric films on the surfaces. The polymerizations are believed to result from the heat generated by the rubbing and, possibly, from catalytic and/or chemical action of the freshly exposed surface. A specific example of such materials is dilinoleic acid and ethylene glycol combinations which can form a polyester frictional polymer film. These materials are known to the art and descriptions of them are found, for example, in the journal "Wear", Volume 26, pages 369–392, and West German Published Patent Application No. 2,339,065. These disclosures are hereby incorporated by reference for their discussions of frictional polymer formers.

Typically these functional additives are known metal or amine salts of organo sulfur, phosphorus, boron or carboxylic acids which are the same as or of the same type as used in oil-based fluids. Typically such salts are of carboxylic acids of 1 to 22 carbon atoms including both aromatic and aliphatic acids; sulfur acids such as alkyl and aromatic sulfonic acids and the like; phosphorus acids such as phosphoric acid, phosphorus acid, phosphinic acid, acid phosphate esters and analogous sulfur homologs such as the thiophosphoric and dithiophosphoric acid and related acid esters; boron acids include boric acid, acid borates and the like. Useful functional additives also include metal dithiocarbamates such as molybdenum and antimony dithiocarbamates; as well as dibutyl tin sulfide, tributyl tin oxide, phosphates and phosphites; borate amine salts, chlorinated waxes; trialkyl tin oxide, molybdenum phosphates, and chlorinated waxes.

Many such functional additives are known to the art. For example, descriptions of additives useful in conventional oil-based systems and in the aqueous systems of this invention are found in "Advances in Petroleum Chemistry and Refining", Volume 8, edited by John J. McKetta, Interscience Publishers, New York, 1963, pages 31–38 inclusive; Kirk-Othmer "Encyclopedia of Chemical Technology", Volume 12, Second Edition, Interscience Publishers, New York, 1967, page 575 et seq.; "Lubricant Additives" by M. W. Ranney, Noyes Data Corporation, Park Ridge, N.J., U.S.A., 1973; and "Lubricant Additives" by C. V. Smalheer and R. K. Smith, The Lezius-Hiles Co., Cleveland, Ohio, U.S.A. These references are hereby incorporated by reference for their disclosures of functional additives useful in the compositions of this invention.

In certain of the typical aqueous compositions of the invention, the functional additive is a sulfur or chlorosulfur extreme pressure agent, known to be useful in oil-base systems. Such materials include chlorinated aliphatic hydrocarbons, such as chlorinated wax; organic sulfides and polysulfides, such as benzyl-disulfide, bis-(chlorobenzyl)disulfide, dibutyl tetrasulfide, sulfurized sperm oil, sulfurized methyl ester of oleic acid, sulfurized alkylphenol, sulfurized dipentene, sulfurized terpene, and sulfurized Diels-Alder adducts; phosphosulfurized hydrocarbons, such as the reaction product of phosphorus sulfide with turpentine or methyl oleate; phosphorus esters such as the dihydrocarbon and trihydrocarbon phosphites, i.e., dibutyl phosphite, diheptyl phosphite, dicyclohexyl phosphite, pentylphenyl phosphite, dipentylphenyl phosphite, tridecyl phosphite, distearyl phosphite and polypropylene substituted phenol phosphite; metal thiocarbamates, such as zinc dioctyldithiocarbamate and barium heptylphenol dithiocarbamate; and Group II metal salts of a phosphorodithioic acid, such as zinc dicyclohexyl phosphorodithioate.

The functional additive can also be a film former such as a synthetic or natural latex or emulsion thereof in water. Such latexes include natural rubber latexes and polystyrene butadienes synthetic latex.

The functional additive can also be an anti-chatter or anti-squawk agent. Examples of the former are the amide metal dithiophosphate combinations such as disclosed in West German Pat. No. 1,109,302; amine salt-azomethene combinations such as disclosed in British Patent Specification no. 893,977; or amine dithiophosphate such as disclosed in U.S. Pat. No. 3,002,014. Examples of anti-squawk agents are N-acyl-sarcosines and derivatives thereof such as disclosed in U.S. Pat. Nos. 3,156,652 and 3,156,653; sulfurized fatty acids and esters thereof such as disclosed in U.s. Pat. Nos. 2,913,415 and 2,982,734; and esters of dimerized fatty acids such as disclosed in U.S. Pat. No. 3,039,967. The above-cited patents are incorporated herein by reference for their disclosure as pertinent to anti-chatter and anti-squawk agents useful as a functional additive in the aqueous systems of the present invention.

Specific examples of functional additives useful in the aqueous systems of this invention include the following commercially available products.

TABLE I

| Functional Additive Tradename | Chemical Description | Supplier |
| --- | --- | --- |
| Anglamol 32 | Chlorosulfurized hydrocarbon | Lubrizol[1] |
| Anglamol 75 | Zinc dialkyl phosphate | Lubrizol[1] |
| Molyvan L | A thiaphosphomolybdate | Vanderbilt[2] |
| Lubrizol-5315 | Sulfurized cyclic carboxylate ester | Lubrizol[1] |
| Emcol TS 230 | Acid phosphate ester | Witco[3] |

[1]The Lubrizol Corporation, Wickliffe, Ohio, U.S.A.
[2]R.T. Vanderbilt Company, Inc., New York, N.Y., U.S.A.
[3]Witco Chemical Corp., Organics Division, Houston, Texas, U.S.A.

Mixtures of two or more of any of the aforedescribed functional additives can also be used.

Typically, a functionally effective amount of the functional additive is present in the aqueous compositions of this invention.

The term "functionally effective amount" refers to a sufficient quantity of an additive to impart desired properties intended by the addition of said additive. For example, if an additive is a rust-inhibitor, a functionally effective amount of said rust-inhibitor would be an amount sufficient to increase the rust-inhibiting characteristics of the composition to which it is added. Similarly, if the additive is an anti-wear agent, a functionally effective amount of said anti-wear agent would be a sufficient quantity of the anti-wear agent to improve the anti-wear characteristics of the composition to which it is added.

The aqueous systems of this invention often contain at least one inhibitor for corrosion of metals. These inhibitors can prevent corrosion of either ferrous or non-ferrous metals (e.g., copper, bronze, brass, titanium, aluminum and the like) or both. The inhibitor can be organic or inorganic in nature. Usually it is sufficiently soluble in water to provide a satisfactory inhibiting action though it can function as a corrosion-inhibitor without dissolving in water, it need not be water-soluble. Many suitable inorganic inhibitors useful in the aqueous systems of the present invention are known to those skilled in the art. Included are those described in "Protective Coatings for Metals" by Burns and Bradley, Reinhold Publishing Corporation, Second Edition, Chapter 13, pages 596-605. This disclosure relative to inhibitors are hereby incorporated by reference. Specific examples of useful inorganic inhibitors include alkali metal nitrites, sodium di- and tripolyphosphate, potassium and dipotassium phosphate, alkali metal borate and mixtures of the same. Many suitable organic inhibitors are known to those of skill in the art. Specific examples include hydrocarbyl amine and hydroxy-substituted hydrocarbyl amine neutralized acid compound, such as neutralized phosphates and hydrocarbyl phosphate esters, neutralized fatty acids (e.g., those having about 8 to about 22 carbon atoms), neutralized aromatic carboxylic acids (e.g., 4-tertiarybutyl benzoic acid), neutralized naphthenic acids and neutralized hydrocarbyl sulfonates. Mixed salt esters of alkylated succinimides are also useful. Particularly useful amines include the alkanol amines such as ethanol amine, diethanolamine. Mixtures of two or more of any of the afore-described corrosion-inhibitors can also be used. The corrosion-inhibitor is usually present in concentrations in which they are effective in inhibiting corrosion of metals with which the aqueous composition comes in contact.

Certain of the aqueous systems of the present invention (particularly those that are used in cutting or shaping of metal) can also contain at least one polyol with inverse solubility in water. Such polyols are those that become less soluble as the temperature of the water increases. They thus can function as surface lubricity agents during cutting or working operations since, as the liquid is heated as a result of friction between a metal workpiece and worktool, the polyol of inverse solubility "plates out" on the surface of the workpiece, thus improving its lubricity characteristics.

The aqueous systems of the present invention can also include at least one bactericide. Such bactericides are well known to those of skill in the art and specific examples can be found in the aforementioned McCutcheon publication "Functional Materials" under the heading "Antimicrobials" on pages 9-20 thereof. This disclosure is hereby incorporated by reference as it relates to suitable bactericides for use in the aqueous compositions or systems of this invention. Generally, these bactericides are water-soluble, at least to the extent to allow them to function as bactericides.

The aqueous systems of the present invention can also include such other materials as dyes, e.g., an acid green dye; water softeners, e.g., ethylene diamine tetraacetate sodium salt or nitrilo triacetic acid; odor masking agents, e.g., citronella, oil of lemon, and the like; and anti-foamants, such as the well-known silicone anti-foamant agents.

The aqueous systems of this invention may also include an anti-freeze additive where it is desired to use the composition at a low temperature. Materials such as ethylene glycol and analogous polyoxyalkylene polyols can be used as anti-freeze agents. Clearly, the amount used will depend on the degree of anti-freeze protection desired and will be known to those of ordinary skill in the art.

It should also be noted that many of the ingredients described above for use in making the aqueous systems of this invention are industrial products which exhibit or confer more than one property on such aqueous compositions. Thus, a single ingredient can provide several functions thereby eliminating or reducing the need for some other additional ingredient. Thus, for example, an extreme pressure agent such as tributyl tin oxide can also function as a bactericide.

We claim:

1. A borated amine salt of at least one dihydrocarbyl monothiophosphoric acid wherein the borated amine salt is derived from an amine having the general formula

$$R^3R^4R^5N$$

wherein each of $R^3$, $R^4$, $R^5$ are independently hydrogen, hydrocarbyl, aminohydrocarbyl, hydroxyhydrocarbyl or hydroxy hydrocarbyloxyhydrocarbyl groups or $R^3$ and $R^4$ are hydrocarbyl groups joined together to form a ring including the nitrogen and optionally sulfur, phosphorus, oxygen, or other nitrogen atoms, said amine containing at least one hydroxyl or N—H group, and

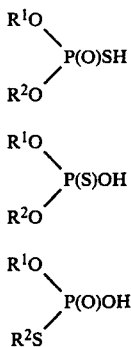

or mixtures thereof wherein $R^1$ and $R^2$ are each independently hydrocarbyl groups containing from 1 to about 30 carbon atoms.

2. The borated amine salt of claim 1 wherein a total number of carbon atoms in $R^1$ and $R^2$ is at least about 4.

3. The salt of claim 1 wherein $R^3$ and $R^4$ are hydrogen and $R^5$ is a hydrocarbyl group.

4. The salt of claim 1 derived from at least one hydroxyhydrocarbyl amine.

5. The salt of claim 4 wherein the hydroxyhydrocarbyl amine is an alkoxylated hydrocarbylamine of the formula

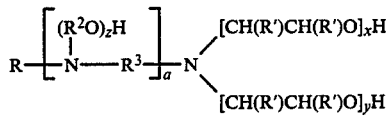

wherein R is a hydrocarbyl group containing from about 6 to about 30 carbon atoms, $R^2$ is an ethylene or propylene group, $R^3$ is an alkylene group containing up to about 5 carbon atoms, a is zero or 1, each R' is hydrogen or a lower alkyl group, and x, y and z are each independently integers from zero to about 10, at least one of x, y and z being at least 1.

6. The borated amine salt of claim 1 derived from a nitrogen-containing composition prepared by the reaction of a hydrocarbon-substituted carboxylic acid-producing compound with at least about one-half equivalent, per equivalent of acid producing compound, of an amine containing at least one hydrogen attached to a nitrogen atom.

7. The borated amine salt of claim 6 wherein the amine is a polyamine.

8. The borated amine salt of claim 1 derived from a boron- and nitrogen-containing composition prepared by forming an acylated nitrogen intermediate by reaction of a hydrocarbon-substituted carboxylic acid-producing compound with at least about one-half equivalent, per equivalent of acid-producing compound, of an amine containing at least one hydrogen attached to a nitrogen atom, and reacting said intermediate with a boron compound.

9. The borated amine salt of claim 8 wherein the amine is a polyamine.

10. The borated amine salt of claim 8 wherein the amount of boron compound reacted with the intermediate is sufficient to provide from about 0.1 to about 10 atomic proportion of boron for each atomic proportion of nitrogen in the intermediate.

11. A lubricant or functional fluid composition selected from the group consisting of automatic transmission fluids, transaxle lubricants, gear lubricants, metal-working lubricants and hydraulic fluids comprising a major amount of at least one oil of lubricating viscosity and a minor amount of (A) the borated amine salt of claim 1.

12. A lubricant or functional fluid selected from the group consisting of automatic transmission fluids, transaxle lubricants, gear lubricants, metal-working lubricants and hydraulic fluids of claim 11 wherein the composition also contains (B) at least one soluble nitrogen-containing composition prepared by the reaction of a hydrocarbon-substituted succinic acid-producing compound with at least about one-half equivalent, per equivalent of acid-producing compound, of an amine containing at least one hydrogen attached to a nitrogen atom.

13. The composition of claim 12 wherein the amine of (B) is a polyamine.

14. The composition of claim 12 wherein the succinic acid-producing compound of (B) contains an average of at least about 50 aliphatic carbon atoms in the substituent.

15. The composition of claim 12 wherein the succinic acid-producing compound of (B) is selected from the group consisting of succinic acids, anhydrides, esters and halides.

16. The composition of claim 12 wherein the hydrocarbon substituent of the succinic acid-producing compound of (B) is derived from a polyolefin having an Mn value within the range of from about 700 to about 10,000.

17. The composition of claim 12 wherein the amine of (B) is characterized by the formula $$R_1R_2NH$$

wherein $R_1$ and $R_2$ are each independently hydrogen, or hydrocarbon, amino-substituted hydrocarbon, hydroxysubstituted hydrocarbon, alkoxy-substituted hydrocarbon, amino, carbamyl, thiocarbamyl, guanyl, and acylimidoyl groups provided that only one of $R_1$ and $R_2$ may be hydrogen.

18. The composition of claim 12 wherein the amine of (B) is a polyamine.

19. The composition of claim 12 wherein the weight ratio of A:B is from about 0.1:1 to about 10:1.

20. The lubricant or functional fluid composition selected from the group consisting of automatic transmission fluids, transaxle lubricants, gear lubricants, metal-working lubricants and hydraulic fluids of claim 12 wherein the soluble nitrogen-containing composition (B) also contains boron and is prepared by the reaction of the soluble acylated nitrogen compound with at least one boron compound selected from the class consisting of boron trioxide, boron halides, boron acids, boron anhydrides, boron amides and esters of boron acids.

21. The lubricant composition of claim 11 wherein the composition is a lubricating oil or a grease.

22. An aqueous system comprising at least about 40% water and at least one borated amine salt of claim 1.

23. The aqueous system of claim 22 also containing (B) at least one soluble nitrogen-containing composition prepared by the reaction of a hydrocarbon-substituted succinic acid-producing compound with at least about one-half equivalent, per equivalent of acid-producing compound, of an amine containing at least one hydrogen attached to a nitrogen atom.

24. A borated amine salt of at least one dihydrocarbyl monothiophosphoric acid prepared by reacting a dialkylphosphite of the following formula $$\begin{array}{c} R^1O \\ \phantom{R^1O}\diagdown \\ \phantom{R^1O\diagdown}P(O)H \\ \phantom{R^1O\diagdown P}\diagup \\ R^2O \end{array} \quad (IV)$$

wherein $R^1$ and $R^2$ are each independently hydrocarbyl groups containing from 1 to about 30 carbon atoms, a sulfur source, an amine, and a boron compound wherein the molar ratio of phosphite:sulfur source:amine:boron compound is about 1:0.4–1:0.4–1:0.5–5.

25. The borated amine salt of claim 24 wherein the sulfur source is elemental sulfur, a sulfur halide, or a sulfurized organic compound.

26. The borated amine salt of claim 24 wherein the sulfur source is elemental sulfur.

27. The borated amine salt of claim 24 wherein the amine is characterized by the formula $$R^3R^4R^5N$$

wherein each of $R^3R^4R^5$ are independently hydrogen, hydrocarbyl, aminohydrocarbyl, hydroxyhydrocarbyl or hydroxyhydrocarbyloxyhydrocarbyl groups or $R^3$ and $R^4$ are hydrocarbyl groups joined together to form a ring including the nitrogen and optionally sulfur, oxygen, phosphorus, or other nitrogen atoms, said amine containing at least one hydroxyl or N—H group.

28. The borated amine salt of claim 27 wherein $R^3$ and $R^4$ are hydrogen and $R^5$ is a hydrocarbyl group.

29. The borated amine salt of claim 24 wherein the amine is at least one hydroxy amine.

30. The borated amine salt of claim 29 wherein the hydroxy amine is an alkoxylated hydrocarbyl amine of the formula $$R{-}{\left[{-}\underset{\underset{\displaystyle R^3}{|}}{N}{-}{-}R^3{-}\right]}_a{-}N{\diagup}^{[CH(R')CH(R')O]_xH}_{\diagdown[CH(R')CH(R')O]_yH}$$

(with $(R^2O)_zH$ substituent)

wherein R is a hydrocarbyl group containing from about 6 to about 30 carbon atoms, $R^2$ is an ethylene or propylene group, $R^3$ is an alkylene group containing up to about 5 carbon atoms, a is zero or 1, each R' is hydrogen or a lower alkyl group, and x, y and z are each independently integers from zero to about 10, at least one of x, y and z being at least 1.

31. The borated amine salt of claim 24 wherein the amine is a nitrogen-containing composition prepared by the reaction of a hydrocarbon-substituted carboxylic acid-producing compound with at least about one-half equivalent, per equivalent of acid-producing compound, of an amine containing at least one hydrogen attached to a nitrogen atom.

32. The borated amine salt of claim 31 wherein the amine is a polyamine.

33. The borated amine salt of claim 24 derived from a boron- and nitrogen-containing composition prepared by forming an acylated nitrogen intermediate by reaction of a hydrocarbon-substituted carboxylic acid-producing compound with at least about one-half equivalent, per equivalent of acid-producing compound, of an amine containing at least one hydrogen attached to a nitrogen atom, and reacting said intermediate with a boron compound.

34. The borated amine salt of claim 33 wherein the amine is a polyamine.

35. The borated amine salt of claim 33 wherein the amount of boron compound reacted with the intermediate is sufficient to provide from about 0.1 to about 10 atomic proportion of boron for each atomic proportion of nitrogen in the intermediate.

36. The borated amine salt of claim 24 wherein the boron compound selected from a class consisting of boron trioxide, boron halides, boron acids, boron anhydrides, boron amides and esters of boron acids.

37. The borated amine salt of claim 24 wherein the amine and the boron compound are prereacted to form a borated amine salt prior to mixing with the phosphite and sulfur source.

38. The borated amine salt of claim 24 wherein the phosphite, sulfur source and amine are reacted to form an amine salt which is thereafter borated with a boron compound.

39. A lubricant or functional fluid composition selected from the group consisting of automatic transmission fluids, transaxle lubricants, gear lubricants, metalworking lubricants and hydraulic fluids comprising a major amount of at least one oil of lubricating viscosity and a minor amount of (A) the borated amine salt of claim 24.

40. The lubricant or functional fluid composition selected from the group consisting of automatic transmission fluids, transaxle lubricants, gear lubricants, metal-working lubricants and hydraulic fluids of claim 39 wherein the composition also contains (B) at least one soluble nitrogen-containing composition prepared by the reaction of a hydrogen-substituted succinic acid-producing compound with at least about one-half equivalent, per equivalent of acid-producing compound, of an amine containing at least one hydrogen attached to a nitrogen atom.

41. The composition of claim 40 wherein the amine of (B) is a polyamine.

42. The composition of claim 40 wherein the succinic acid-producing compound of (B) contains an average of at least about 50 aliphatic carbon atoms in the substituent.

43. The composition of claim 40 wherein the succinic acid-producing compound of (B) is selected from the group consisting of succinic acids, anhydrides, esters and halides.

44. The composition of claim 40 wherein the hydrocarbon substituent of the succinic acid-producing compound of (B) is derived from a polyolefin having an Mn value within the range of from about 700 to about 10,000.

45. The composition of claim 40 wherein the amine of (B) is characterized by the formula $$R_1R_2NH$$

wherein $R_1$ and $R_2$ are each independently hydrogen, or hydrocarbon, amino-substituted hydrocarbon, hydroxy-substituted hydrocarbon, alkoxy-substituted hydrocarbon, amino, carbamyl, thiocarbamyl, guanyl, and acylimidoyl groups provided that only one of $R_1$ and $R_2$ may be hydrogen.

46. The composition of claim 40 wherein the amine of (B) is a polyamine.

47. The composition of claim 40 wherein the weight ratio of A:B is from about 0.1:1 to about 10:1.

48. The lubricant or functional fluid selected from the group consisting of automatic transmission fluids, transaxle lubricants, gear lubricants, metal-working lubricants and hydraulic fluids of claim 40 wherein the soluble nitrogen-containing composition (B) also contains boron and is prepared by the reaction of the soluble nitrogen-containing composition (B) with at least one boron compound selected from the group consisting of boron trioxide, boron halides, boron acids, boron anhydrides, boron amides and ester of boron acids.

49. The lubricant composition of claim 39 wherein the composition is a lubricating oil or a grease.

50. An aqueous system comprising at least about 40% water and at least one borated amine salt of claim 24.

51. A borated amine salt of at least one dihydrocarbyl monothiophosphoric acid prepared by reacting at least one dihydrocarbyl monothiophosphoric acid, an amine and a boron compound wherein the molar ratio of dihydrocarbyl monothiophosphoric acid:amine:boron compound is from 1:0.4–1:0.5–5.

52. The borated amine salt of claim 51 wherein the monothiophosphoric acid is reacted with the amine to form an amine salt which is thereafter borated with the boron compound.

53. The borated amine salt of claim 51 wherein the amine and boron compound are prereacted to form a borated amine which is then reacted with the monothiophosphoric acid.

54. A lubricant or functional fluid composition selected from the group consisting of automatic transmission fluids, transaxle lubricants, gear lubricants, metal-working lubricants and hydraulic fluids comprising a major amount of at least one oil of lubricating viscosity and a minor amount of (A) the borated amine salt of claim 51.

55. The lubricant composition of claim 54 wherein the composition is a lubricating oil or a grease.

56. An aqueous system comprising at least about 40% water and at least one borated amine salt of claim 51.

* * * * *